*(12)* United States Patent
Genet et al.

US006497730B1

(10) Patent No.: US 6,497,730 B1
(45) Date of Patent: Dec. 24, 2002

(54) CATIONIC METHYLENEDIOXY BENZENES, THEIR USE FOR OXIDATION DYEING OF KERATIN FIBERS, DYEING COMPOSITIONS AND METHODS

(75) Inventors: Alain Genet, Aulnay-sous-Bois (FR); Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/646,644

(22) PCT Filed: Jan. 14, 2000

(86) PCT No.: PCT/FR00/00076

§ 371 (c)(1),
(2), (4) Date: Nov. 21, 2000

(87) PCT Pub. No.: WO00/43388

PCT Pub. Date: Jul. 27, 2000

(30) Foreign Application Priority Data

Jan. 21, 1999  (FR) ............................................ 99 00635

(51) Int. Cl.[7] .................................................. A61K 7/13
(52) U.S. Cl. ...................... 8/405; 8/405; 8/406; 8/409; 8/410; 8/412; 8/421; 8/426; 548/311.7; 548/311.1; 548/311.4; 549/29; 549/37
(58) Field of Search ............................ 8/405, 406, 409, 8/410, 411, 412, 421, 426; 548/311.7, 311.1, 311.4; 549/29, 37

(56) References Cited

U.S. PATENT DOCUMENTS

| | | | |
|---|---|---|---|
| 4,003,699 A | 1/1977 | Rose et al. ..................... | 8/409 |
| 4,823,985 A | 4/1989 | Grollier et al. ................ | 222/1 |
| 4,865,617 A | 9/1989 | Junino et al. .................. | 8/409 |
| 4,975,092 A | 12/1990 | Chan et al. .................... | 8/408 |
| 5,061,289 A | 10/1991 | Clausen et al. ................ | 8/405 |
| 5,380,340 A | 1/1995 | Neunhoeffer et al. .......... | 8/409 |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| EP | 0 424 525 | 5/1991 |
| FR | 2 586 913 | 3/1987 |
| FR | 2 603 483 | 3/1988 |
| FR | 2 733 749 | 11/1996 |
| FR | 2 750 048 | 12/1997 |
| GB | 1 026 978 | 4/1966 |
| GB | 1 153 196 | 5/1969 |
| JP | 2-19576 | 1/1990 |
| WO | WO 94/08969 | 4/1994 |
| WO | WO 94/08970 | 4/1994 |
| WO | WO 96/15765 | 5/1996 |

OTHER PUBLICATIONS

Co–pending Application No. 09/646,643; Attorney Docket No. 05725.0765–00000Title: Novel Cationic Di–methylene-dioxy–benzenes, Their Use for Oxidation Dyeing of Keratin Fibres Inventor(s):Alain Genet et al. U.S. Filing Date: Nov. 21, 2000.
English language Derwent Abstract of DE 195 43 988.
English language Derwent Abstract of FR 2 733 749.
English language Derwent Abstract of FR 2 750 048.
English language Derwent Abstract of JP 2–19576.

*Primary Examiner*—Yogendra N. Gupta
*Assistant Examiner*—Eisa B Elhilo
(74) *Attorney, Agent, or Firm*—Finnegan, Henderson, Farabow, Garrett & Dunner, L.L.P.

(57) ABSTRACT

The invention relates to novel methylene-dioxybenzenes comprising at least one cationic group Z, Z being chosen from quaternized aliphatic chains, aliphatic chains comprising at least one quaternized saturated ring and aliphatic chains comprising at least one quaternized unsaturated ring, to their use as oxidation dye precursors for the oxidation dyeing of keratin fibres, to dye compositions containing them and to oxidation dyeing processes using them.

41 Claims, No Drawings

CATIONIC METHYLENEDIOXY BENZENES, THEIR USE FOR OXIDATION DYEING OF KERATIN FIBERS, DYEING COMPOSITIONS AND METHODS

The invention relates to novel methylene-dioxybenzenes comprising at least one cationic group Z, Z being chosen from quaternized aliphatic chains, aliphatic chains comprising at least one quaternized saturated ring and aliphatic chains comprising at least one quaternized unsaturated ring, to their use as oxidation dye precursors for the oxidation dyeing of keratin fibres, to dye compositions containing them and to oxidation dyeing processes using them.

It is known practice to dye keratin fibres, and in particular human hair, with dye compositions containing oxidation dye precursors, in particular para-phenylenediamines, ortho-aminophenols or para-aminophenols and heterocyclic compounds such as diaminopyrazole derivatives, which are generally referred to as oxidation bases. The oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain hetero-cyclic compounds such as, for example, indole couplers.

The variety of molecules used as oxidation bases and couplers makes it possible to obtain a wide range of colours.

The so-called "permanent" coloration obtained by means of these oxidation dyes must moreover satisfy a certain number of requirements. Thus, it must have no toxicological drawbacks and it must allow shades of the desired-strength to be obtained and have good resistance to external agents (light, bad weather, washing, permanent-waving, perspiration and friction).

The dyes must also allow white hairs to be covered, and, lastly, they must be as unselective as possible, i.e. they must allow the smallest possible differences in coloration to be produced over the entire length of the same keratin fibre, which may indeed be differently sensitized (i.e. damaged) between its tip and its root.

Now, the Applicant has just discovered, entirely surprisingly and unexpectedly, that a novel family of methylene-dioxybenzenes of formula (I) defined below, comprising at least one cationic group Z, Z being chosen from quaternized aliphatic chains, aliphatic chains comprising at least one quaternized saturated ring and aliphatic chains comprising at least one quaternized unsaturated ring, are suitable for use as oxidation dye precursor for oxidation dyeing, but also allow dye compositions to be obtained which lead to strong colorations, in a wide range of shades, and which have excellent properties of resistance to the various treatments to which keratin fibres may be subjected. Lastly, these compositions prove to be readily synthesizable.

These discoveries form the basis of the present invention.

A first subject of the invention is thus methylenedioxy-benzenes of formula (I) below, and the addition salts thereof with an acid:

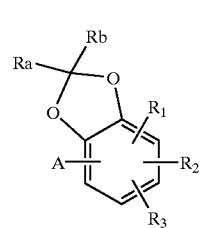

in which:

Ra and Rb, which may be identical or different, can represent a hydrogen atom, a $C_1$–$C_6$ alkyl radical, a $C_1$–$C_6$ hydroxyalkyl radical or can form, together with the carbon atom to which they are attached, a saturated 5-, 6- or 7-membered carbon-based ring;

$R_1$, $R_2$ and $R_3$, which may be identical or different, represent a hydrogen atom; a halogen atom; a group Z as defined below; a group A' as defined below; a ($C_1$–$C_6$) alkylcarbonyl radical; an amino($C_1$–$C_6$)alkylcarbonyl radical; an N—Z-amino($C_1$–$C_6$)alkylcarbonyl radical; an N—($C_1$–$C_6$)alkylamino($C_1$–$C_6$)alkylcarbonyl radical; an N,N-di($C_1$–$C_6$)alkylamino($C_1$–$C_6$)alkylcarbonyl radical; an amino($C_1$–$C_6$)alkylcarbonyl($C_1$–$C_6$)alkyl radical; an N—Z-amino($C_1$–$C_6$)alkylcarbonyl($C_1$–$C_6$)alkyl radical; an N—($C_1$–$C_6$)alkylamino($C_1$–$C_6$)alkylcarbonyl($C_1$–$C_6$) alkyl radical; an N,N-di($C_1$–$C_6$)alkylamino($C_1$–$C_6$) alkylcarbonyl($C_1$–$C_6$)alkyl radical; a carboxyl radical; a ($C_1$–$C_6$)alkylcarboxyl radical; a $C_1$–$C_6$ alkylsulphonyl radical; an aminosulphonyl radical; an N—Z-aminosulphonyl radical; a $C_1$–$C_6$N-alkylaminosulphonyl radical; an N,N-di($C_1$–$C_6$)alkylaminosulphonyl radical; a $C_1$–$C_6$aminosulphonylalkyl radical; a $C_{1-C6}$ N—Z-aminosulphonylalkyl radical; an N—($C_1$–$C_6$) alkylaminosulphonyl ($C_1$–$C_6$)alkyl radical; an N,N-di ($C_1$–$C_6$)alkylaminosulphonyl($C_1$–$C_6$)alkyl radical; a carbamyl radical; an N—($C_1$–$C_6$)alkylcarbamyl radical; an N,N-di($C_1$–$C_6$)alkylcarbamyl radical; a carbamyl ($C_1$–$C_6$)alkyl radical; an N—($C_1$–$C_6$)alkylcarbamyl ($C_1$–$C_6$)alkyl radical; an N,N-di($C_1$–$C_6$)alkylcarbamyl ($C_1$–$C_6$)alkyl radical; a $C_1$–$C_6$ alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; a $C_1$–$C_6$ trifluoroalkyl radical; a cyano radical; a group $OR_6$ or $SR_6$; a $C_1$–$C_6$ aminoalkyl radical in which the alkyl is unsubstituted or substituted with one or more hydroxyl radicals; an amino($C_1$–$C_6$)alkyl radical in which the alkyl is unsubstituted or substituted with one or more hydroxyl radicals and in which the amine is substituted with one or two identical or different radicals chosen from alkyl, $C_1$–$C_6$ monohydroxyalkyl, $C_2$–$C_6$ polyhydroxyalkyl, ($C_1$–$C_6$)alkylcarbonyl, carbamyl, N—($C_1$–$C_6$) alkylcarbamyl or N,N-di($C_1$–$C_6$)alkylcarbamyl, $C_1$–$C_6$ alkylsulphonyl, formyl, trifluoro($C_1$–$C_6$)alkylcarbonyl, ($C_1$–$C_6$)alkylcarboxyl and thiocarbamyl radicals, or from the groups Z defined below, or which are able to form, with the nitrogen atom to which they are attached, a 5- or 6-membered carbon-based ring or a ring containing one or more hetero atoms;

$R_6$ denotes a $C_1$–$C_6$ alkyl radical; a $C_1$–$C_6$ monohydroxy-alkyl radical; a $C_2$–$C_6$ polyhydroxyalkyl radical; a group Z; a ($C_1$–$C_6$)alkoxy($C_1$–$C_6$)alkyl radical; an aryl radical; a benzyl radical; a carboxy($C_1$–$C_6$)alkyl radical; a ($C_1$–$C_6$)alkylcarboxy-($C_1$–$C_6$)alkyl radical; a cyano ($C_1$–$C_6$)alkyl radical; a carbamyl($C_1$–$C_6$)alkyl radical; an N—($C_1$–$C_6$)alkylcarbamyl ($C_1$–$C_6$)alkyl radical; an N,N- di($C_1$–$C_6$)alkylcarbamyl ($C_1$–$C_6$)alkyl radical; a $C_1$–$C_6$ trifluoroalkyl radical; a $C_1$–$C_6$ aminosulphonylalkyl radical; a $C_1$–$C_6$ N—Z-aminosulphonylalkyl radical; an N—($C_1$–$C_6$)alkylaminosulphonyl($C_1$–$C_6$)alkyl radical; an N,N-di($C_1$–$C_6$)alkylaminosulphonyl($C_1$–$C_6$)alkyl radical; a ($C_1$–$C_6$)alkylsulphinyl($C_1$–$C_6$)alkyl radical; a ($C_1$–$C_6$)alkylsulphonyl($C_1$–$C_6$)alkyl radical; a ($C_1$–$C_6$) alkylcarbonyl($C_1$–$C_6$)alkyl radical; a $C_1$–$C_6$ aminoalkyl radical; a $C_1$–$C_6$ aminoalkyl radical in which the alkyl is unsubstituted or substituted with one or more hydroxyl radicals and in which the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$)alkylcarbonyl, formyl, trifluoro-($C_1$–$C_6$)alkylcarbonyl, ($C_1$–$C_6$)alkylcarboxyl, carbamyl, N—($C_1$–$C_6$)alkylcarbamyl, N,N-di-($C_1$–$C_6$) alkylcarbamyl, thiocarbamyl and $C_1$–$C_6$ alkylsulphonyl radicals, and from the groups Z; or which are able to form, together with the nitrogen atom to which they are attached, a 5- or 6-membered carbon-based ring or a ring containing one or more hetero atoms;

A represents a group —$NR_4R_5$ or a hydroxyl radical;

A' represents a group —$NR'_4R'_5$ or a hydroxyl radical;

$R_4$, $R_5$, $R'_4$ and $R'_5$, which may be identical or different, represent a hydrogen atom; a group Z; a $C_1$–$C_6$alkyl radical; a $C_1$–$C_6$ monohydroxyalkyl radical; a $C_2$–$C_6$ polyhydroxyalkyl radical; a ($C_1$–$C_6$)alkoxy($C_1$–$C_6$)alkyl radical; an aryl radical; a benzyl radical; a cyano($C_1$–$C_6$) alkyl radical; a carbamyl($C_1$–$C_6$)alkyl radical; an N—($C_1$–$C_6$)alkylcarbamyl($C_1$–$C_6$)alkyl radical; an N,N-di($C_1$–$C_6$)alkylcarbamyl($C_1$–$C_6$)alkyl radical; a thiocarbamyl($C_1$–$C_6$)alkyl radical; a $C_1$–$C_6$ trifluoroalkyl radical; a $C_1$–$C_6$ sulphoalkyl radical; a ($C_1$–$C_6$) alkylcarboxy($C_1$–$C_6$)alkyl radical; a ($C_1$–$C_6$) alkylsulphinyl($C_1$–$C_6$)alkyl radical; a $C_1$–$C_6$ aminosulphonylalkyl radical; a $C_1$–$C_6$ N—Z-aminosulphonylalkyl radical; an N—($C_1$–$C_6$)alkylaminosulphonyl($C_1$–$C_6$) alkyl radical; an N,N-di($C_1$–$C_6$)alkylaminosulphonyl ($C_1$–$C_6$)alkyl radical; a ($C_1$–$C_6$)alkylcarbonyl($C_1$–$C_6$) alkyl radical; a $C_1$–$C_6$ aminoalkyl radical in which the alkyl is unsubstituted or substituted with one or more hydroxyl radicals; a $C_1$–$C_6$ aminoalkyl radical in which the alkyl is unsubstituted or substituted with one or more hydroxyl radicals and in which the amine is substituted with one or two identical or different radicals chosen from $C_1$–$C_6$ alkyl, $C_1$–$C_6$ monohydroxyalkyl, $C_2$–$C_6$ polyhydroxyalkyl, ($C_1$–$C_6$)alkylcarbonyl, carbamyl, N—($C_1$–$C_6$)alkylcarbamyl, N,N-di($C_1$–$C_6$) alkylcarbamyl, ($C_1$–$C_6$)alkylsulphonyl, formyl, trifluoro ($C_1$–$C_6$)alkylcarbonyl, ($C_1$–$C_6$)alkylcarboxyl and thiocarbamyl radicals, or from the groups Z, or which are able to form, together with the nitrogen atom to which they are attached, a 5- or 6-membered carbon-based ring or a ring containing one or more hetero atoms;

Z is chosen from the unsaturated cationic groups of formulae (II) and (III) below, and the saturated cationic groups of formula (IV) below:

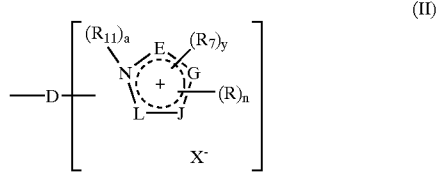

(II)

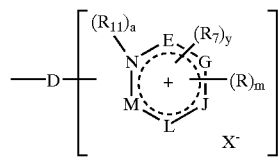

(III)

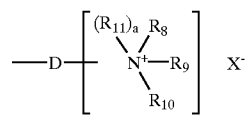

(IV)

in which:

D is a linker arm which represents a linear or branched alkyl chain preferably containing from 1 to 14 carbon atoms, which can be interrupted by one or more hetero atoms such as oxygen, sulphur or nitrogen atoms, and which can be substituted with one or more hydroxyl or $C_1$–$C_6$ alkoxy radicals, and which can bear one or more ketone functions;

the ring members E, G, J, L and M, which may be identical or different, represent a carbon, oxygen, sulphur or nitrogen atom;

n is an integer between 0 and 4 inclusive;

m is an integer between 0 and 5 inclusive;

the radicals R, which may be identical or different, represent a second group Z which is identical to or different from the first group Z, a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano($C_1$–$C_6$) alkyl radical, a $C_1$–$C_6$ alkoxy radical, a tri($C_1$–$C_6$) alkylsilane($C_1$–$C_6$)alkyl radical, an amido radical, an aldehydo radical, a carboxyl radical, a ($C_1$–$C_6$) alkylcarbonyl radical, a thio radical, a $C_1$–$C_6$ thioalkyl radical, a $C_1$–$C_6$ alkylthio radical, an amino radical, an amino radical protected with a ($C_1$–$C_6$)alkylcarbonyl, carbamyl or $C_1$–$C_6$ alkylsulphonyl radical; a group NHR" or NR" R'" in which R" and R'", which may be identical or different, represent a $C_1$–$C_6$ alkyl radical, a $C_1$–$C_6$ monohydroxyalkyl radical or a $C_2$–$C_6$ polyhydroxyalkyl radical;

$R_7$ represents a $C_1$–$C_6$ alkyl radical, a $C_1$–$C_6$ monohydroxyalkyl radical, a $C_2$–$C_6$ polyhydroxyalkyl radical, a cyano($C_1$–$C_6$)alkyl radical, a tri($C_1$–$C_6$)alkylsilane ($C_1$–$C_6$)alkyl radical, a ($C_1$–$C_6$)alkoxy($C_1$–$C_6$)alkyl radical, a carbamyl($C_1$–$C_6$)alkyl radical, a ($C_1$–$C_6$) alkylcarboxy($C_1$–$C_6$)alkyl radical, a benzyl radical or a second group Z which is identical to or different from the first group Z;

$R_8$, $R_9$ and $R_{10}$, which may be identical or different, represent a $C_1$–$C_6$ alkyl radical, a $C_1$–$C_6$ monohydroxyalkyl radical, a $C_2$–$C_6$ polyhydroxyalkyl radical, a ($C_1$–$C_6$)alkoxy($C_1$–$C_6$)alkyl radical, a cyano($C_1$–$C_6$) alkyl radical, an aryl radical, a benzyl radical, a $C_1$–$C_6$ amidoalkyl radical, a tri($C_1$–$C_6$)alkylsilane($C_1$–$C_6$) alkyl radical or a $C_1$–$C_6$ aminoalkyl radical in which the amine is protected with a ($C_1$–$C_6$)alkylcarbonyl, carbamyl or $C_1$–$C_6$ alkylsulphonyl radical; two of the radicals $R_8$, $R_9$ and $R_{10}$ can together also form, with the nitrogen atom to which they are attached, a saturated 5- or 6-membered carbon-based ring or a ring containing one or more hetero atoms such as, for example, a pyrrolidine ring, a piperidine ring, a piperazine ring or a morpholine ring, it being possible for the said ring to be unsubstituted or substituted with a halogen atom, a hydroxyl radical, a $C_1$–$C_6$ alkyl radical, a $C_1$–$C_6$ monohydroxyalkyl radical, a $C_2$–$C_6$ polyhydroxyalkyl radical, a nitro radical, a cyano radical, a cyano($C_1$–$C_6$) alkyl radical, a $C_1$–$C_6$ alkoxy radical, a tri($C_1$–$C_6$)alkylsilane($C_1$–$C_6$)alkyl radical, an amido radical, an aldehydo radical, a carboxyl radical, a keto($C_1$–$C_6$) alkyl radical, a thio radical, a $C_1$–$C_6$ thioalkyl radical, a $C_1$–$C_6$ alkylthio radical, an amino radical or an amino radical protected with a ($C_1$–$C_6$)alkylcarbonyl, carbamyl or $C_1$–$C_6$ alkylsulphonyl radical;

one of the radicals $R_8$, $R_9$ and $R_{10}$ can also represent a second group Z which is identical to or different from the first group Z;

$R_{11}$ represents a $C_1$–$C_6$ alkyl radical; a $C_1$–$C_6$ monohydroxyalkyl radical; a $C_2$–$C_6$ polyhydroxyalkyl radical; an aryl radical; a benzyl radical; a $C_1$–$C_6$ aminoalkyl radical, a $C_1$–$C_6$ aminoalkyl radical in which the amine is protected with a ($C_1$–$C_6$)alkylcarbonyl, carbamyl or $C_1$–$C_6$ alkylsulphonyl radical; a carboxy($C_1$–$C_6$)alkyl radical; a cyano($C_1$–$C_6$)alkyl radical; a carbamyl ($C_1$–$C_6$)alkyl radical; a $C_1$–$C_6$ trifluoroalkyl radical; a tri($C_1$–$C_6$)alkylsilane($C_1$–$C_6$)alkyl radical; a $C_1$–$C_6$ sulphonamidoalkyl radical; a ($C_1$–$C_6$)alkylcarboxy ($C_1$–$C_6$)alkyl radical; a ($C_1$–$C_6$)alkylsulphinyl($C_1$–$C_6$) alkyl radical; a ($C_1$–$C_6$)alkylsulphonyl($C_1$–$C_6$)alkyl radical; a ($C_1$–$C_6$)alkylketo($C_1$–$C_6$)alkyl radical; an N—($C_1$–$C_6$)alkylcarbamyl($C_1$–$C_6$)alkyl radical; an N—($C_1$–$C_6$)alkylsulphonamido($C_1$–$C_6$)alkyl radical;

a and y are integers equal to 0 or 1; with the following conditions:

in the unsaturated cationic groups of formula (II):
when a=0, the linker arm D is attached to the nitrogen atom,
when a=1, the linker arm D is attached to one of the ring members E, G, J or L,
y can take the value 1 only:
1) when the ring members E, G, J and L simultaneously represent a carbon atom and when the radical $R_7$ is borne by the nitrogen atom of the unsaturated ring; or alternatively
2) when at least one of the ring members E, G, J and L represents a nitrogen atom to which the radical $R_7$ is attached;

in the unsaturated cationic groups of formula (III):
when a=0, the linker arm D is attached to the nitrogen atom,
when a=1, the linker arm D is attached to one of the ring members E, G, J, L or M,
y can take the value 1 only when at least one of the ring members E, G, J, L and M represents a divalent atom and when the radical $R_7$ is borne by the nitrogen atom of the unsaturated ring;

in the cationic groups of formula (IV):
when a=0, then the linker arm D is attached to the nitrogen atom bearing the radicals $R_8$ to $R_{10}$,
when a=1, then two of the radicals $R_8$ to $R_{10}$ form, together with the nitrogen atom to which they are attached, a saturated 5- or 6-membered ring as defined above, and the linker arm D is borne by a carbon atom of the said saturated ring;

$X^-$ represents a monovalent or divalent anion and is preferably chosen from a halogen atom such as chlorine, bromine, fluorine or iodine, a hydroxide, a hydrogen sulphate or a $C_1$–$C_6$ alkyl sulphate such as, for example, a methyl sulphate or an ethyl sulphate;

it being understood that:
the number of cationic groups Z is at least equal to 1.

As mentioned above, the colorations obtained with the oxidation dye composition in accordance with the invention are strong and produce a wide range of shades and colours. They moreover have excellent properties of resistance to the action of various external agents (light, bad weather, washing, permanent-waving, perspiration, friction). These properties are particularly noteworthy, in particular as regards the resistance of the colorations obtained to the action of light, washing and perspiration.

In formulae (I), (II), (III) and (IV) above, the alkyl and alkoxy radicals can be linear or branched.

Among the carbon-based rings which may be formed, together with the radicals Ra and Rb, mention may be made particularly of pentane, hexane and heptane rings.

Among the rings of the unsaturated groups Z of formula (II) above, mention may be made in particular, for example, of pyrrole, imidazole, pyrazole, oxazole, thiazole and triazole rings.

Among the rings of the unsaturated groups Z of formula (III) above, mention may be made in particular, for example, of pyridine, pyrimidine, pyrazine, oxazine and triazine rings.

The compounds of formula (I) above are preferably chosen from:

1-[2-(benzo[1,3]dioxol-5-ylamino)ethyl]-3-methyl-3H-imidazol-1-ium chloride;
1- [2-(6-hydroxybenzo[1,3]dioxol-5-ylamino)ethyl]-3-methyl-3H-imidazol-1-ium chloride;
1-[2-(6-methoxybenzo[1,3]dioxol-5-ylamino)ethyl]-3-methyl-3H-imidazol1-ium chloride;
1-[2-(6-ethoxybenzo[1,3]dioxol-5-ylamino)ethyl]-3-methyl-3H-imidazol-1-ium chloride;
1-{2-[6-(2-hydroxyethoxy)benzo[1,3]dioxol-5-yl-amino]ethyl}-3-methyl-3H-imidazol-1-ium chloride;
1-[2-(6-aminobenzo[1,3]dioxol-5-ylamino)ethyl]-3-methyl-3H-imidazol-1-ium chloride;
1-{2-[6-(2-(3-methyl-3H-imidazol-1-ium)ethoxy)-benzo[1,3]dioxol-5-ylamino]ethyl}-3-methyl-3H-imidazol-1-ium dichloride;
1-[2-(6-aminobenzo[1,3]dioxol-5-yloxy)ethyl]-3-methyl-3H-imidazol-1-ium chloride;
1-[3-(6-aminobenzo[1,3]dioxol-5-yloxy)propyl]-3-methyl-3H-imidazol-1-ium chloride;
[2-(6-aminobenzo[1,3]dioxol-5-yloxy)ethyl]diethyl-(2-hydroxyethyl)ammonium bromide;
[2-(6-aminobenzo[1,3]dioxol-5-yloxy)ethyl]diethyl-methylammonium methyl sulphate;
1-[2-(6-aminobenzo[1,3]dioxol-5-yloxy)ethyl]-1,4-dimethylpiperazin-1-ium chloride;
1-[2-(2,2-bis(hydroxymethyl)-6-methoxybenzo[1,3]-dioxol-5-ylamino)ethyl]-3-methyl-3H-imidazol-1-ium chloride;

and the addition salts thereof with an acid.

The addition salts with an acid of the compounds of formula (I) in accordance with the invention are preferably chosen from the hydrochlorides, hydrobromides, sulphates, citrates, succinates, tartrates, lactates and acetates.

The compounds of formula (I) in accordance with the invention can readily be obtained according to methods that are well known in the prior art, for example by reduction of the corresponding cationic nitro compounds when these compounds bear an amino group.

This reduction step (production of a primary aromatic amine), which may or may not be followed by a salification, is generally, for convenience, the final step of the synthesis.

This reduction can take place earlier in the sequence of reactions leading to the preparation of the compounds of formula (I), and according to well-known processes it is then necessary to "protect" the primary amine created (for example by an acetylation, formylation, benzenesulphonation, etc. step), then carry out the desired substitution(s) or modification(s) (including quaternization) and end by "deprotecting" (generally in acidic medium) the amine function.

Similarly, the phenolic function can be protected according to well-known processes with a benzyl radical ("deprotection" by catalytic reduction) or with an acetyl or mesyl radical ("deprotection" in acidic medium).

The cationic chains are themselves obtained by methods that are well known in the prior art.

The production of the quaternized amines can be carried out, for example:

in one step, by condensation of a methylenedioxybenzene compound comprising a haloalkyl radical with a compound bearing a tertiary amine radical, or by condensation of a methylenedioxybenzene compound comprising a tertiary amine radical with a compound bearing a haloalkyl radical, or by quaternization of a methylenedioxybenzene compound comprising a tertiary amine radical with an alkylating agent;

or in two steps, by condensation of a methylenedioxybenzene compound comprising a haloalkyl radical with a compound bearing a secondary amine, followed by quaternization with an alkylating agent.

The haloalkyl radicals borne by the intermediate methylenedioxybenzene compounds can be prepared by methods that are well known in the prior art, in one or more steps, for/example by condensation of a dihaloalkyl compound with an amine or a hydroxyl, or by halogenation of a hydroxyalkyl chain.

When the synthesis is complete, the compounds of formula (I) in accordance with the invention can, if necessary, be recovered by methods which are well known in the state of the art, such as crystallization or distillation.

Another subject of the invention is the use of the compounds of formula (I) in accordance with the invention as oxidation dye precursor for the oxidation dyeing of keratin fibres, and in particular of human keratin fibres such as the hair.

The invention also relates to a composition for the oxidation dyeing of keratin fibres, and in particular of human keratin fibres such as the hair, characterized in that it comprises as oxidation dye, in a medium which is suitable for dyeing, at least one compound of formula (I) in accordance with the invention.

The compound(s) of formula (I) in accordance with the invention preferably represent(s) from 0.0005% to 12% by weight approximately relative to the total weight of. the dye composition, and even more preferably from 0.005% to 6% by weight approximately relative to this weight.

The medium which is suitable for dyeing (or the support) generally consists of water or a mixture of water and at least one organic solvent. As organic solvent, mention may be made, for example, of $C_1$–$C_4$ lower alkanols, such as ethanol and isopropanol; glycerol; glycols and glycol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, similar products and mixtures thereof.

The solvents can be present in proportions preferably of between 1 and 40% by weight approximately relative to the total weight of the dye composition, and even more preferably between 5 and 30% by weight approximately.

The pH of the dye composition in accordance with the invention is generally between 3 and 12 approximately, and preferably between 5 and 11 approximately. It can be adjusted to the desired value using acidifying or basifying agents commonly used to dye keratin fibres.

Among the acidifying agents which may be mentioned, for example, are inorganic or organic acids such as hydrochloric acid, orthophosphoric acid, sulphuric acid, carboxylic acids such as acetic acid, tartaric acid, citric acid and lactic acid, and sulphonic acids.

Among the basifying agents which may be mentioned, for example, are aqueous ammonia, alkaline carbonates, alkanolamines such/as mono-, di- and triethanolamine and derivatives thereof, sodium hydroxide, potassium hydroxide and the compounds of formula (V) below:

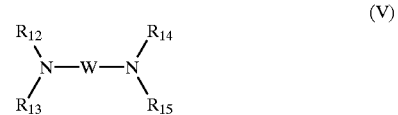

(V)

in which W is a propylene residue optionally substituted with a hydroxyl group or a $C_1$–$C_6$ alkyl radical; $R_{12}$, $R_{13}$, $R_{14}$ and $R_{15}$, which may be identical or different, represent a hydrogen atom, a $C_1$–$C_6$ alkyl radical or a $C_1$–$C_6$ hydroxyalkyl radical.

In addition to the compound(s) of formula (I) defined above, the dye composition in accordance with the invention can also contain at least one oxidation base which may be chosen from the oxidation bases conventionally used for oxidation dyeing and among which mention may be made in particular of para-phenylenediamines, bis(phenyl)alkylenediamines, para-aminophenols, ortho-aminophenols and heterocyclic bases.

Among the para-phenylenediamines which can be mentioned more particularly, for example, are para-phenylenediamine, para-tolylenediamine, 2-chloro-para-penylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyl-para-phenylenediamine, 2-β-acetylaminoethyloxy-para-phenylenediamine and N-(β-methoxyethyl)-para-phenylenediamine, and the addition salts thereof with an acid.

Among the bis(phenyl)alkylenediamines which can be mentioned more particularly, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4- methylaminophenyl)tetramethylenediamine, N,N'-bis (ethyl)-N,N'-bis(4'-amino-3'-methylphenyl)-ethylenediamine and 1,8-bis(2,5-diaminophenoxy)-3,5-dioxaoctane, and the addition salts thereof with an acid.

Among the para-aminophenols which can be mentioned more particularly, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols which can be mentioned more particularly, for example, are 2-aminophenol, 2-amino-5-methylphenol, 2-amino-6-methylphenol and 5-acetamido-2-aminophenol, and the addition salts thereof with an acid.

Among the heterocyclic bases which can be mentioned more particularly, for example, are pyridine derivatives, pyrimidine derivatives and pyrazole derivatives.

Among the pyridine derivatives which may be mentioned more particularly are the compounds described, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine/derivatives which may be mentioned more particularly are the compounds described, for example, in German patent DE 2 359 399 or Japanese patents JP 88-169 571 and JP 96-10659 or patent application Wo 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminoprazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino)ethanol, 5,6-dimethylpyrazolo[1,5-a]pyrimidine-3,7-diamine, 2,6-dimethylpyrazolo[1,5-a]pyrimidine-3,7-diamine and 2,5,N7,N7-tetramethylpyrazolo[1,5-a]pyrimidine-3,7-diamine and 3-amino-5-methyl-7-imidazolylpropyl-aminopyrazolo[1,5-a]pyrimidine, the tautomeric forms thereof, when a tautomeric equilibrium exists, and the addition salts thereof with an acid.

Among the pyrazole derivatives which may be mentioned more particularly are the compounds described in patents DE 3 843 892 and DE 4 133 957 and patent applications WO 94/08969, WO 94/08970, FR-A-2 733 749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropyl-pyrazole, 4-amino-5-(2'-aminoethyl)amino-1,3-dimethyl-pyrazole, 3,4,5-triaminopyrazole, 1-methyl-3,4,5-triaminopyrazole, 3,5-diamino-1-methyl-4-methylamino-pyrazole and 3,5-diamino-4-(β-hydroxyethyl)amino-1-methylpyrazole, and the addition salts thereof with an acid.

When they are used, these oxidation bases preferably represent from 0.0005% to 12% by weight approximately relative to the total weight of the dye composition, and even more preferably from 0.005% to 6% by weight approximately relative to this weight.

The oxidation dye compositions in accordance with the invention can also contain one or more couplers and/or one or more direct dyes, in particular to modify the shades or to enrich them with glints.

The couplers which can be used in the oxidation dye compositions in accordance with the invention can be chosen from the couplers used conventionally in oxidation dyeing and among which mention may be made in particular of meta-phenylene-diamines, meta-aminophenols and meta-diphenols and heterocyclic couplers such as, for example, indole derivatives, indoline derivatives, pyridine derivatives and pyrazolones, and the addition salts thereof with an acid.

These couplers are chosen more particularly from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxy-benzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one, and the addition salts thereof with an acid.

When they are present, these couplers preferably represent from 0.0001 to 10% by weight approximately relative to the total weight of the dye composition and even more preferably from 0.005 to 5% by weight approximately relative to this weight.

In general, the addition salts with an acid which can be used in the context of the invention (compounds of formula (I), oxidation bases and couplers) are chosen in particular from the hydrochlorides, hydrobromides, sulphates, citrates, succinates, tartrates, lactates and acetates.

The dye composition in accordance with the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, packaging agents such as, for example, silicones, film-forming agents, preserving agents and opacifiers.

Needless to say, a person skilled in the art will take care to select this or these optional additional compounds such that the advantageous properties intrinsically associated with the oxidation dye composition in accordance with the invention are not, or are not substantially, adversely affected by the addition(s) envisaged.

The dye composition according to the invention can be in various forms, such as in the form of liquids, creams or gels or in any other form which is suitable for dyeing keratin fibres, and in particular human hair.

The invention also relates to a process for dyeing keratin fibres, and in particular human keratin fibres such as the hair, using the dye composition as defined above.

A subject of the invention is also a process for the oxidation dyeing of keratin fibres, and in particular of human keratin fibres such as the hair, using the dye composition as defined above.

According to this process, at least one dye composition as defined above is applied to the fibres, for a period which is sufficient to develop the desired coloration, either in air or using an oxidizing agent. The dye composition can optionally contain oxidation catalysts, in order to accelerate the oxidation process.

According to a first embodiment of the process of the invention, the coloration of the fibres can be carried out without adding an oxidizing agent, merely by contact with atmospheric oxidation.

According to a second embodiment of the process of the invention, and in particular when the dye composition in accordance with the invention contains one or more oxidation bases and/or one or more couplers, at least one dye composition as defined above is applied to the fibres, the colour being developed at acidic, neutral or alkaline pH using an oxidizing agent which is added to the dye composition just at the time of use, or which is present in an oxidizing composition which is applied simultaneously or sequentially in a separate manner.

According to this second embodiment of the dyeing process of the invention, the dye composition described above is preferably mixed, at the time of use, with an oxidizing composition containing, in a medium which is suitable for dyeing, at least one oxidizing agent present in an amount which is sufficient to develop a coloration. The mixture obtained is then applied to the keratin fibres and is left in place for 3 to 50 minutes approximately, preferably 5 to 30 minutes approximately, after which the fibres are rinsed, washed with shampoo, rinsed again and dried.

The oxidizing agent present in the oxidizing composition as defined above can be chosen from the oxidizing agents conventionally used for the oxidation dyeing of keratin fibres, and among which mention may be made of hydrogen peroxide, urea peroxide, alkali metal bromates and persalts such as perborates and persulphates, and enzymes such as peroxidases, laccases, tyrosinases and oxidoreductases, among which mention may be made in particular of pyranose oxidases, glucose oxidases, glycerol oxidases, lactate oxidases, pyruvate oxidases and uricases.

The pH of the oxidizing composition containing the oxidizing agent as defined above is such that, after mixing with the dye composition, the pH of the resultant composition applied to the keratin fibres preferably varies between 3 and 12 approximately, and even more preferably between 5 and 11. It is adjusted to the desired value using acidifying or basifying agents commonly used to dye keratin fibres and as defined above.

The oxidizing composition as defined above can also contain various adjuvants conventionally used in compositions for dyeing the hair and as defined above.

The composition which is finally applied to the keratin fibres can be in various forms, such as in the form of liquids, creams, gels or any other form which is suitable for dyeing keratin fibres, and in particular human hair.

Another subject of the invention is a multi-compartment dyeing device or "kit" or any other multi-compartment packaging system, a first compartment of which contains the dye composition as defined above and a second compartment of which contains the oxidizing composition as defined above. These devices can be equipped with a means for delivering the desired mixture onto the hair, such as the devices described in patent FR 2,586,913 in the name of the Applicant.

The examples which follow are intended to illustrate the invention.

PREPARATION EXAMPLE

Preparation Example 1

Synthesis of 1-[2-(6-aminobenzo[1,3]dioxol-5-ylamino)ethyl]-3-methyl-3H-imidazol-1-ium chloride hydrochloride

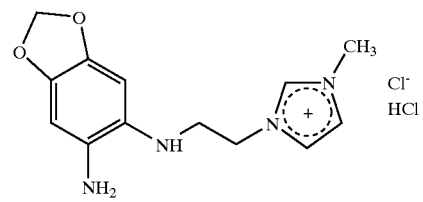

a) Preparation of (2-chloroethyl) (6-nitrobenzo[1,3]dioxol-5-yl)amine

A solution of 50.0 g (0.22 mol) of 2-(6-nitrobenzo[1,3]dioxol-5-ylamino)ethanol (RN 106146-44-5) and 42 ml of triethylamine in 260 ml of dimethyl-formamide was prepared and cooled to a temperature of about 0° C.

20.4 ml (0.263 mol) of mesyl chloride were added dropwise over 40 minutes, while keeping the temperature between 0° C. and 5° C.

The temperature was allowed to rise to about 20° C. and 27.8 g (0.658 mol) of lithium chloride was added (the reaction was exothermic).

The mixture was heated on a boiling water bath for half an hour and poured into 750 g of ice-cold water.

The crystalline precipitate was spin-filtered, reslurried in water and dried.

After recrystallization from refluxing ethyl acetate, 38.9 g of orange-coloured crystals of (2-chloroethyl)(6-nitrobenzo[1,3]dioxol-5-yl)amine were obtained, which melted at 120° C. (Kofler) and the elemental analysis of which, calculated for $C_9H_9N_2O_4Cl$, was:

|  | % | | | | |
| --- | --- | --- | --- | --- | --- |
|  | C | H | N | O | Cl |
| Calculated | 44.19 | 3.71 | 11.45 | 26.16 | 14.49 |
| Found | 44.31 | 3.70 | 11.68 | 26.40 | 14.30 | b) Preparation of 3-methyl-1-[2-(6-nitrobenzo[1,3]dioxol-5-ylamino)ethyl]-3H-imidazol-1-ium chloride A mixture of 48.9 g (0.2 mol) of (2-chloro-ethyl)(6-nitrobenzo[1,3]dioxol-5-yl)amine obtained above in the preceding step and 49.3 g (0.6 mol) of 1-methyl-1H-imidazole in 100 ml of toluene was refluxed for 8 hours.

The mixture was cooled and the crystalline precipitate was spin-filtered.

After purification by recrystallization from a refluxing mixture of 96° ethanol and water, 52.7 g of orange-coloured crystals of 3-methyl-1-(2-(6-nitro-benzo[1,3]dioxol-5-ylamino)ethyl]-3H-imidazol-1-ium chloride were obtained, which melted at a temperature of 203° C. (Kofler) and the elemental analysis of which, calculated for $C_{13}H_{15}N_4O_4Cl \cdot \frac{1}{2} H_2O$, was:

|  | % | | | | |
| --- | --- | --- | --- | --- | --- |
|  | C | H | N | O | Cl |
| Calculated | 46.51 | 4.80 | 16.69 | 21.44 | 10.56 |
| Found | 46.22 | 4.78 | 15.98 | 21.76 | 10.59 | c) Reduction of 3-methyl-1-[2-(6-nitrobenzo[1,3]dioxol-5-ylamino)ethyl]-3H-imidazol-1-ium chloride 52.0 g (0.159 mol) of the compound obtained above in the preceding step, 15 g of 5% palladium-on-charcoal (containing 50% water), 300 ml of 96° ethanol and 300 ml of water were placed in a hydrogenator.

The reduction took place over ½ an hour under a hydrogen pressure of about 8 bar and at a temperature which was gradually raised to 70° C.

After filtering off the catalyst under nitrogen, the mixture was poured into 60 ml of 36% hydrochloric acid and the filtrate was evaporated to dryness under reduced pressure.

The compound was taken up several times in absolute ethanol. After recrystallization from a refluxing ethanol/water mixture and drying at 40° C. under vacuum and over potassium hydroxide, 29.3 g of pale grey crystals of 1-[2-(6-aminobenzo[1,3]dioxol-5-ylamino)ethyl]-3-methyl-3H-imidazol-1-ium chloride hydrochloride were obtained, which melted with decomposition at 238–240° C. (Kofler) and the elemental analysis of which, calculated for $C_{13}H_{18}N_4O_2Cl_2$, was:

|  | % | | | | |
| --- | --- | --- | --- | --- | --- |
|  | C | H | N | O | Cl |
| Calculated | 46.86 | 5.44 | 16.81 | 9.60 | 21.28 |
| Found | 46.59 | 5.44 | 18.26 | 10.15 | 21.38 |

APPLICATION EXAMPLES

Example 1 of Dyeing in Air

At the time of use, the dye composition below in accordance with the invention was prepared:

| 1-[2-(6-Aminobenzo[1,3]dioxol-5-ylamino)ethyl]-3-methyl-3H-imidazol-1-ium chloride hydrochloride (compound of formula (I)) | 1.0 g |
| --- | --- |
| 96° ethanol | 20 g |
| $NH_4OH/NH_4Cl$ (1M/1M) pH 9.5 buffer | 10 g |
| Demineralized water qs | 100 g |

This composition was applied to locks of permanent-waved grey hair containing 90% white hairs, and the coloration was allowed to develop for 30 minutes, without adding any oxidizing agent other than atmospheric oxygen.

The hair was then rinsed, washed with a standard shampoo, rinsed again and then dried.

The hair was dyed in an iridescent coppery blond shade.

Example 2 of Dyeing in a Neutral Medium

The dye composition below in accordance with the invention was prepared:

| 1-[2-(6-Aminobenzo[1,3]dioxol-5-ylamino)ethyl]-3-methyl-3H-imidazol-1-ium chloride hydrochloride (compound of formula (I)) | 1.0 g |
| --- | --- |
| 96° ethanol | 18 g |
| $K_2HPO_4/KH_2PO_4$ (1.5M/1M) buffer | 10 g |
| Sodium metabisulphite | 0.68 g |
| Pentasodium salt of diethylene-triaminepentaacetic acid | 1.1 g |
| Demineralized water qs | 100 g |

At the time of use, the above dye composition was mixed weight for weight with a 20-volumes hydrogen peroxide solution (6% by weight) of pH 3.

The mixture obtained was applied to locks of permanent-waved grey hair containing 90% white hairs, for 30 minutes. The locks were then rinsed, washed with a standard shampoo, rinsed again and then dried.

The hair was dyed in a pale golden iridescent blond shade.

Example 3 of Enzymatic Dyeing

The ready-to-use dye composition below was prepared:

| 1-[2-(6-Aminobenzo[1,3]dioxol-5-ylamino)ethyl]-3-methyl-3H-imidazol-1-ium chloride hydrochloride (compound of formula (I)) | 1.0 g |
| --- | --- |
| 96° ethanol | 10 g |
| Uricase from *Arthrobacter globiformis* at a concentration of 20 International Units (I.U.)/mg, sold by the company Sigma | 1.0 g |
| Uric acid | 1.0 g |
| Monoethanolamine qs | pH = 9.5 |
| Demineralized water qs | 100 g |

The ready-to-use dye composition described above was applied to locks of natural grey hair containing 90% white hairs, for 30 minutes. The hair was then rinsed, washed with a standard shampoo and then dried.

The hair was dyed in an iridescent coppery blond shade.

What is claimed is:
1. A compound of formula (I) or an acid addition salt thereof:

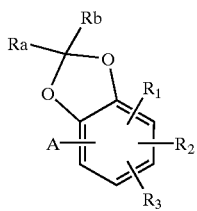
(I)

wherein:
Ra and Rb, which may be identical or different, are each chosen from hydrogen, $C_1$–$C_6$ alkyl groups, $C_1$–$C_6$ hydroxyalkyl groups, and together can form, with the carbon atom to which they are attached, a saturated ring chosen from 5-, 6- and 7-membered carbon-based rings;

$R_1$, $R_2$ and $R_3$, which may be identical or different, are each chosen from hydrogen; halogens; Z groups; A' groups; ($C_1$–$C_6$)alkylcarbonyl groups; amino($C_1$–$C_6$)alkylcarbonyl groups; N—Z-amino($C_1$–$C_6$)alkylcarbonyl groups; N—($C_1$–$C_6$)alkylamino($C_1$–$C_6$)alkylcarbonyl groups; N,N-di($C_1$–$C_6$)alkylamino($C_1$–$C_6$)alkylcarbonyl groups; amino($C_1$–$C_6$)alkylcarbonyl($C_1$–$C_6$)alkyl groups; N—Z-amino($C_1$–$C_6$)alkylcarbonyl($C_1$–$C_6$)alkyl groups; N—($C_1$–$C_6$)alkylamino($C_1$–$C_6$)-alkylcarbonyl($C_1$–$C_6$)alkyl groups; N,N-di($C_1$–$C_6$)alkylamino($C_1$–$C_6$)alkylcarbonyl-($C_1$–$C_6$)alkyl groups; a carboxyl group; ($C_1$–$C_6$)alkylcarboxyl groups; $C_1$–$C_6$ alkylsulphonyl groups; aminosulphonyl groups; N—Z-aminosulphonyl groups; $C_1$–$C_6$ N-alkyl-aminosulphonyl groups; N,N-di($C_1$–$C_6$)alkylaminosulphonyl groups; $C_1$–$C_6$ aminosulphonylalkyl groups; $C_1$–$C_6$ N—Z-aminosulphonylalkyl groups; N—($C_1$–$C_6$)alkylaminosulphonyl($C_1$–$C_6$)alkyl groups; N,N-di($C_1$–$C_6$)alkylaminosulphonyl($C_1$–$C_6$)alkyl groups; a carbamyl group; N—($C_1$–$C_6$)alkylcarbamyl groups; N,N-di($C_1$–$C_6$)alkylcarbamyl groups; carbamyl($C_1$–$C_6$)alkyl groups; N—($C_1$–$C_6$)alkylcarbamyl($C_1$–$C_6$)alkyl groups; N,N-di($C_1$–$C_6$)alkylcarbamyl($C_1$–$C_6$)alkyl groups; $C_1$–$C_6$ alkyl groups; $C_1$–$C_6$ monohydroxyalkyl groups; $C_2$–$C_6$ polyhydroxyalkyl groups; ($C_1$–$C_6$)alkoxy($C_1$–$C_6$)alkyl groups; $C_1$–$C_6$ trifluoroalkyl groups; a cyano group; groups —$OR_5$; groups —$SR_6$; $C_1$–$C_6$ aminoalkyl groups wherein said alkyl is optionally substituted with at least one hydroxyl group; amino($C_1$–$C_6$)alkyl groups wherein said alkyl component is optionally substituted with at least one hydroxyl group and wherein said amino is substituted with one or two groups, which may be identical or different, chosen from alkyl groups, $C_1$–$C_6$ monohydroxyalkyl groups, $C_2$–$C_6$ polyhydroxyalkyl groups, ($C_1$–$C_6$)alkylcarbonyl groups, a carbamyl group, N—($C_1$–$C_6$)alkylcarbamyl groups, N,N-di($C_1$–$C_6$)alkylcarbamyl groups, ($C_1$–$C_6$)alkylsulphonyl groups, a formyl group, ftrifluoro($C_1$–$C_6$)alkylcarbonyl groups, ($C_1$–$C_6$)alkylcarboxyl groups, a thiocarbamyl group, and Z groups, and said substituted amino may constitute a ring chosen from 5 and 6-membered rings containing at least one heteroatom wherein one of said at least one heteroatoms is the nitrogen atom of said amino;

$R_6$ is chosen from $C_1$–$C_6$ alkyl groups; $C_1$–$C_6$ monohydroxyalkyl groups; $C_2$–$C_6$ polyhydroxyalkyl groups; a group Z;($C_1$–$C_6$)alkoxy($C_1$–$C_6$)alkyl groups; aryl groups; a benzyl group; carboxy($C_1$–$C_6$)alkyl groups; ($C_1$–$C_6$)alkylcarboxy-($C_1$–$C_6$)alkyl groups; cyano ($C_1$–$C_6$)alkyl groups; carbamyl($C_1$–$C_6$)alkyl groups; N—($C_1$–$C_6$)alkylcarbamyl($C_1$–$C_6$)alkyl groups; N,N-di($C_1$–$C_6$)alkylcarbamyl($C_1$–$C_6$)alkyl groups; $C_1$–$C_6$ trifluoroalkyl groups; $C_1$–$C_6$ aminosulphonylalkyl groups; $C_1$–$C_6$ N—Z-aminosulphonylalkyl groups; N—($C_1$–$C_6$)alkylaminosulphonyl($C_1$–$C_6$)alkyl groups; N,N-di($C_1$–$C_6$)alkylaminosulphonyl($C_1$–$C_6$)alkyl groups; ($C_1$–$C_6$)alkylsulphinyl($C_1$–$C_6$)alkyl groups; ($C_1$–$C_6$)alkylsulphonyl($C_1$–$C_6$)alkyl groups;($C_1$–$C_6$)alkylcarbonyl($C_1$–$C_6$)alkyl groups; $C_1$–$C_6$ aminoalkyl groups; $C_1$–$C_6$ aminoalkyl groups wherein said alkyl is optionally substituted with at least one hydroxyl group and wherein said amino is substituted with one or two groups, which may be identical or different, chosen from $C_1$–$C_6$ alkyl groups, $C_1$–$C_6$ monohydroxyalkyl groups, $C_2$–$C_6$ polyhydroxyalkyl groups, ($C_1$–$C_6$) alkylcarbonyl groups, a formyl group, trifluoro-($C_1$–$C_6$)alkylcarbonyl groups, ($C_1$–$C_6$)alkylcarboxyl groups, a carbamyl group, N—($C_1$–$C_6$)alkylcarbamyl groups, N,N-di-($C_1$–$C_6$)alkylcarbamyl groups, a thiocarbamyl group, $C_1$–$C_6$ alkylsulphonyl groups, Z groups, and said substituted amino may constitute a ring chosen from 5- and 6-membered rings containing at least one heteroatom wherein one of said at least one heteroatoms is the nitrogen atom of said amino:

A is chosen from —$NR_4R_5$ groups and a hydroxyl group;

A' is chosen from —$NR'_4R'_5$ groups and a hydroxyl group;

$R_4$, $R_5$, $R'_4$ and $R'_5$, which may be identical or different, are each chosen from hydrogen; Z groups; $C_1$–$C_6$ alkyl groups; $C_1$–$C_6$ monohydroxyalkyl groups; $C_2$–$C_6$ polyhydroxyalkyl groups; ($C_1$–$C_6$)alkoxy($C_1$–$C_6$)alkyl groups; aryl groups; a benzyl group; cyano($C_1$–$C_6$) alkyl groups; carbamyl($C_1$–$C_6$)alkyl groups; N—($C_1$–$C_6$)alkylcarbamyl($C_1$–$C_6$)alkyl groups; N,N-di($C_1$–$C_6$)alkylcarbamyl($C_1$–$C_6$)alkyl groups; thiocarbamyl($C_1$–$C_6$)alkyl groups; $C_1$–$C_6$ trifluoroalkyl groups; $C_1$–$C_6$ sulphoalkyl groups; ($C_1$–$C_6$) alkylcarboxy($C_1$–$C_6$)alkyl groups; ($C_1$–$C_6$) alkylsulphinyl($C_1$–$C_6$)alkyl groups; $C_1$–$C_6$ aminosulphonylalkyl groups; $C_1$–$C_6$ N—Z-aminosulphonylalkyl groups; N—($C_1$–$C_6$) alkylaminosulphonyl($C_1$–$C_6$)alkyl groups; N,N-di ($C_1$–$C_6$)alkylaminosulphonyl($C_1$–$C_6$)alkyl groups; ($C_1$–$C_6$)alkylcarbonyl($C_1$–$C_6$)alkyl groups; $C_1$–$C_6$ aminoalkyl groups wherein said alkyl is optionally substituted with at least one hydroxyl group; $C_1$–$C_6$ aminoalkyl groups wherein said alkyl is optionally substituted with at least one hydroxyl group and wherein said amino is substituted with one or two groups, which may be identical or different, chosen from $C_1$–$C_6$ alkyl groups, $C_1$–$C_6$ monohydroxyalkyl groups, $C_2$–$C_6$ polyhydroxyalkyl groups, ($C_1$–$C_6$) alkylcarbonyl groups, a carbamyl group, N—($C_1$–$C_6$) alkylcarbamyl groups, N,N-di($C_1$–$C_6$)alkylcarbamyl groups, ($C_1$–$C_6$)alkylsulphonyl groups, a formyl group, trifluoro($C_1$–$C_6$)alkylcarbonyl groups, ($C_1$–$C_6$) alkylcarboxyl groups, thiocarbamyl groups, groups Z, and said substituted amino may constitute a ring chosen from 5- and 6-membered rings containing at least one, heteroatom wherein one of said at least one heteroatoms is the nitrogen atom of said amino;

Z, which may be identical or different, is chosen from unsaturated cationic groups of formula (II), unsaturated cationic groups of formula (III), and saturated cationic groups of formula (IV):

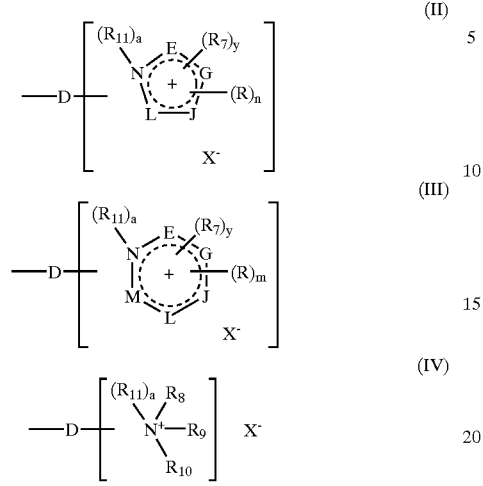

wherein:
D is a linker arm chosen from linear and branched divalent alkyl chains, wherein said linear and branched divalent alkyl chains can be interrupted by at least one heteroatom, and further wherein said linear and branched divalent alkyl chains can be substituted with at least one group chosen from a hydroxyl group and $C_1$–$C_6$ alkoxy groups, further wherein said linear and branched divalent alkyl chains can bear at least one ketone function;
ring members E, G, J, L and M, which may be identical or different, are each chosen from carbon, oxygen, sulphur and nitrogen;
n is an integer ranging from 0 to 4 inclusive;
m is an integer ranging from 0 to 5 inclusive;
the groups R, which may be identical or different, are each chosen from additional Z groups which may be identical to or different from other Z groups, halogens, hydroxyl groups, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri($C_1$–$C_6$)alkylsilane($C_1$–$C_6$)alkyl groups, an amido group, an aldehydo group, a carboxyl group, ($C_1$–$C_6$) alkylcarbonyl groups, a thio group, $C_1$–$C_6$ thioalkyl groups, $C_1$–$C_6$ alkylthio groups, an amino group, amino groups protected with at least one group chosen from ($C_1$–$C_6$)alkylcarbonyl groups, a carbamyl group, and $C_1$–$C_6$ alkylsulphonyl groups, and NHR" groups and NR"R'" groups wherein R" and R'", which may be identical or different, are each chosen from $C_1$–$C_6$ alkyl groups, $C_1$–$C_6$ monohydroxyalkyl groups and $C_2$–$C_6$ polyhydroxyalkyl groups;
$R_7$ is chosen from $C_1$–$C_6$ alkyl groups, $C_1$–$C_6$ monohydroxyalkyl groups, $C_2$–$C_6$ polyhydroxyalkyl groups, cyano($C_1$–$C_6$)alkyl groups, tri($C_1$–$C_6$)alkylsilane($C_1$–$C_6$)alkyl groups, ($C_1$–$C_6$)alkoxy($C_1$–$C_6$)alkyl groups, carbamyl-($C_1$–$C_6$)alkyl groups, ($C_1$–$C_6$)alkylcarboxy($C_1$–$C_6$)-alkyl groups, a benzyl group and an additional Z group which may be identical to or different from other Z groups;
$R_8$, $R_9$ and $R_{10}$, which may be identical or different, are each chosen from $C_1$–$C_6$ alkyl groups, $C_1$–$C_6$ monohydroxyalkyl groups, $C_2$–$C_6$ polyhydroxyalkyl groups, ($C_1$–$C_6$)alkoxy($C_1$–$C_6$)alkyl groups, cyano($C_1$–$C_6$)alkyl groups, aryl groups, a benzyl group, $C_1$–$C_6$ amidoalkyl groups, tri($C_1$–$C_6$) alkylsilane($C_1$–$C_6$)alkyl groups, and $C_1$–$C_6$ aminoalkyl groups wherein said amino is protected with at least one group chosen from ($C_1$–$C_6$) alkylcarbonyl groups, a carbamyl group and $C_1$–$C_6$ alkylsulphonyl groups; two of said groups $R_8$, $R_9$ and $R_{10}$ can together optionally form, with the nitrogen atom to which they are attached, a saturated ring chosen from 5- and 6-membered carbon-based rings containing at least one heteroatom, wherein said ring is optionally substituted with at least one group chosen from halogens, a hydroxyl group, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri($C_1$–$C_6$)alkylsilane($C_1$–$C_6$)alkyl groups, an amido group, an aldehydo group, a carboxyl group, keto($C_1$–$C_6$)alkyl groups, a thio group, $C_1$–$C_6$ thioalkyl groups, $C_1$–$C_6$ alkylthio groups, an amino group, and amino groups protected with at least one group chosen from ($C_1$–$C_6$)alkylcarbonyl groups, a carbamyl group and $C_1$–$C_6$ alkylsulphonyl groups;
one of said groups $R_8$, $R_9$ and $R_{10}$ is optionally an additional Z group which may be identical to or different from other Z groups;
$R_{11}$ is chosen from $C_1$–$C_6$ alkyl groups, $C_1$–$C_6$ monohydroxyalkyl groups, $C_2$–$C_6$ polyhydroxyalkyl groups, aryl groups, a benzyl group, $C_1$–$C_6$ aminoalkyl groups, carboxy($C_1$–$C_6$)alkyl groups, cyano ($C_1$–$C_6$)alkyl groups, carbamyl($C_1$–$C_6$)alkyl groups, $C_1$–$C_6$ trifluoroalkyl groups, tri($C_1$–$C_6$)alkylsilane ($C_1$–$C_6$)alkyl groups, $C_1$–$C_6$ sulphonamidoalkyl groups, ($C_1$–$C_6$)alkylcarboxy($C_1$–$C_6$)alkyl groups, ($C_1$–$C_6$)alkylsulphinyl($C_1$–$C_6$)alkyl groups, ($C_1$–$C_6$) alkylsulphonyl($C_1$–$C_6$)alkyl groups, ($C_1$–$C_6$) alkylketo($C_1$–$C_6$)alkyl groups, N—($C_1$–$C_6$) alkylcarbamyl($C_1$–$C_6$)alkyl groups, N—($C_1$–$C_6$) alkylsulphonamido($C_1$–$C_6$)alkyl groups, and $C_1$–$C_6$ aminoalkyl groups wherein said amino is protected with at least one group chosen from ($C_1$–$C_6$) alkylcarbonyl groups, a carbamyl group and $C_1$–$C_6$ alkylsulphonyl groups; and
a and y, which may be identical or different, are integers chosen from 0 and 1;
$X^-$ is chosen from monovalent anions and divalent anions;
wherein in said compound of formula (I), at least one of $R_1$, $R_2$, $R_3$, and A comprises at least one Z group; and provided that:
when Z is an unsaturated cationic group of formula (II):
if a=0, then said linker arm D is attached to said nitrogen atom other than E, G, J, and L,
if a=1, then said linker arm D is attached to one of said ring members chosen from E, G, J and L,
y=1 only when:
1) said ring members E, G, J, and L are all simultaneously carbon atoms and $R_7$ is attached to said nitrogen atom of the unsaturated ring; or alternatively
2) at least one of the ring members E, G, J, and L is a nitrogen atom to which $R_7$ is attached,
when Z is an unsaturated cationic group of formula (III):
if a=0, then said linker arm D is attached to said nitrogen atom other than E, G, J, L, and M, if a=1, then said linker arm D is attached to one of said ring members chosen from E, G, J, L, and M, y=1 only when at least one of said ring members E, G, J, L and M is a divalent atom and $R_7$ is attached to said nitrogen atom of the unsaturated ring other than E, G, J, L and M; and when Z is a cationic group of formula (IV):
if a=0, then the linker arm D is attached to the nitrogen atom bearing said groups $R_8$, $R_9$ and $R_{10}$;
if a=1, then two of said groups $R_8$, $R_9$ and $R_{10}$ form, together with the nitrogen atom to which they are attached, a saturated ring chosen from a 5- and 6-membered rings as defined above, and said linker arm D is attached to a carbon atom of said saturated ring.

2. The compound or salt thereof according to claim 1, wherein said linear and branched alkyl chains recited for D contain from 1 to 14 carbon atoms.

3. The compound or salt thereof according to claim 1, wherein said at least one heteratom recited for D is chosen from oxygen, nitrogen, and sulphur.

4. The compound or salt thereof according to claim 1, wherein said Ra and Rb together form a carbon-based ring chosen from a pentane ring, a hexane ring and a heptane ring.

5. The compound or salt thereof according to claim 1, wherein said ring of said unsaturated cationic groups Z of formula (II) is chosen from a pyrrole ring, an imidazole ring, a pyrazole ring, an oxazole ring, a thiazole ring and a triazole ring.

6. The compound or salt thereof according to claim 1, wherein said ring of said unsaturated cationic groups Z of formula (III) is chosen from a pyridine ring, a pyrimidine ring, a pyrazine ring, an oxazine ring and a triazine ring.

7. The compound or salt thereof according to claim 1, wherein two of said groups $R_8$, $R_9$ and $R_{10}$ form a ring chosen from a pyrrolidine ring, a piperidine ring, a piperazine ring and a morpholine ring, wherein said ring is optionally substituted with at least one group chosen from halogens, hydroxyl groups, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri($C_1$–$C_6$)alkylsilane($C_1$–$C_6$) alkyl groups, an amido group, an aldehydo group, a carboxyl group, keto($C_1$–$C_6$)alkyl groups, a thio group, $C_1$–$C_6$ thioalkyl groups, $C_1$–$C_6$ alkylthio groups, an amino group, and amino groups protected with at least one group chosen from ($C_1$–$C_6$)alkylcarbonyl groups, a carbamyl group, and $C_1$–$C_6$ alkylsulphonyl groups.

8. The compound or salt thereof according to claim 1, wherein said $X^-$ is chosen from halogens, a hydroxide group, a hydrogen sulphate group and $C_1$–$C_6$ alkyl sulphate groups.

9. The compound chosen from:
1-[2-(benzo[1,3]dioxol-5-ylamino)ethyl]-3-methyl-3H-imidazol-1-ium chloride;
1-[2-(6-hydroxybenzo[1,3]dioxol-5-ylamino)ethyl]-3-methyl-3H-imidazol-1-ium chloride;
1-[2-(6-methoxybenzo[1,3]dioxol-5-ylamino)ethyl]-3-methyl-3H-imidazol-1-ium chloride;
1-[2-(6-ethoxybenzo[1,3]dioxol-5-ylamino)ethyl]-3-methyl-3H-imidazol-1-ium chloride;
1-{2-[6-(2-hydroxyethoxy)benzo[1,3]dioxol-5-ylamino]ethyl}-3-methyl-3H-imidazol-1-ium chloride;
1-[2-(6-aminobenzo[1,3]dioxol-5-ylamino)ethyl]-3-methyl-3H-imidazol-1-ium chloride;
1-{2-[6-(2-(3-methyl-3H-imidazol-1-ium)ethoxy)benzo[1,3]dioxol-5-ylamino]ethyl}-3-methyl-3H-imidazol-1-ium dichloride;
1-[2-(6-aminobenzo[1,3]dioxol-5-yloxy)ethyl]-3-methyl-3H-imidazol-1-ium chloride;
1-[3-(6-aminobenzo[1,3]dioxol-5-yloxy)propyl]-3-methyl-3H-imidazol-1-ium chloride;
[2-(6-aminobenzo[1,3]dioxol-5-yloxy)ethyl]diethyl(2-hydroxyethyl)ammonium bromide;
[2-(6-aminobenzo[1,3]dioxol-5-yloxy)ethyl] diethylmethylammonium methyl sulphate;
1-[2-(6-aminobenzo[1,3]dioxol-5-yloxy)ethyl]-1,4-dimethylpiperazin-1-ium chloride;
1-[2-(2,2-bis(hydroxymethyl)-6-methoxybenzo[1,3]dioxol-5-ylamino)ethyl]-3-methyl-3H-imidazol-1-ium chloride; or at least one acid addition salt thereof; or
a mixture thereof.

10. The compound or salt thereof according to claim 1, wherein said acid addition salt is chosen from a hydrochloride, a hydrobromide, a sulphate, a citrate, a succinate, a tartrate, a lactate and an acetate.

11. At least one oxidation dye precursor chosen from compounds of formula (I) and acid addition salts thereof:

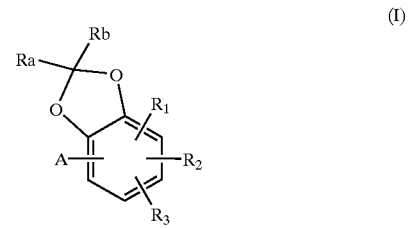

(I)

wherein:
Ra and Rb, which may be identical or different, are each chosen from hydrogen, $C_1$–$C_6$ alkyl groups, $C_1$–$C_6$ hydroxyalkyl groups, and together can form, with the carbon atom to which they are attached, a saturated ring chosen from 5-, 6- and 7-membered carbon-based rings;

$R_1$, $R_2$ and $R_3$, which may be identical or different, are each chosen from hydrogen; halogens Z groups; A' groups; ($C_1$–$C_6$)alkylcarbonyl groups; amino($C_1$–$C_6$)alkylcarbonyl groups; N—Z-amino($C_1$–$C_6$)alkylcarbonyl groups; N—($C_1$–$C_6$)alkylamino($C_1$–$C_6$)alkylcarbonyl groups; N,N-di($C_1$–$C_6$)alkylamino($C_1$–$C_6$)alkylcarbonyl groups; amino($C_1$–$C_6$)alkylcarbonyl($C_1$–$C_6$)alkyl groups; N—Z-amino($C_1$–$C_6$)alkylcarbonyl($C_1$–$C_6$)alkyl groups; N—($C_1$–$C_6$)alkylamino($C_1$–$C_6$)-alkylcarbonyl($C_1$–$C_6$)alkyl groups; N,N-di($C_1$–$C_6$)alkylamino($C_1$–$C_6$)alkylcarbonyl-($C_1$–$C_6$)alkyl groups; a carboxyl group; ($C_1$–$C_6$)alkylcarboxyl groups; $C_1$–$C_6$ alkylsulphonyl groups; aminosulphonyl groups; N—Z-aminosulphonyl groups; $C_1$–$C_6$ N-alkylaminosulphonyl groups; N,N-di($C_1$–$C_6$)alkylaminosulphonyl groups; $C_1$–$C_6$aminosulphonylalkyl groups; $C_1$–$C_6$ N—Z-aminosulphonylalkyl groups; N—($C_1$–$C_6$)alkylaminosulphonyl($C_1$–$C_6$)alkyl groups; N,N-di($C_1$–$C_6$)alkylaminosulphonyl($C_1$–$C_6$)alkyl groups; a carbamyl group; N—($C_1$–$C_6$)alkylcarbamyl groups; N,N-di($C_1$–$C_6$)alkylcarbamyl groups; carbamyl($C_1$–$C_6$)alkyl groups; N—($C_1$–$C_6$)alkylcarbamyl($C_1$–$C_6$)alkyl groups; N,N-di($C_1$–$C_6$)alkylcarbamyl($C_1$–$C_6$)alkyl groups; $C_1$–$C_6$ alkyl groups; $C_1$–$C_6$ monohydroxyalkyl groups; $C_2$–$C_6$ polyhydroxyalkyl groups; ($C_1$–$C_6$)alkoxy($C_1$–$C_6$)alkyl groups; $C_1$–$C_6$ trifluoroalkyl groups; a cyano group; groups —OR$_6$; groups —SR$_6$; C$_1$–C$_6$ aminoalkyl groups wherein said alkyl is optionally substituted with at least one hydroxyl group; amino(C$_1$–C$_6$)alkyl groups wherein said alkyl component is optionally substituted with at least one hydroxyl group and wherein said amino is substituted with one or two groups, which may be identical or different, chosen from alkyl groups, C$_1$–C$_6$ monohydroxyalkyl groups, C$_2$–C$_6$ polyhydroxyalkyl groups, (C$_1$–C$_6$)alkylcarbonyl groups, a carbamyl group, N—(C$_1$–C$_6$)alkylcarbamyl groups, N,N-di(C$_1$–C$_6$)alkylcarbamyl groups, (C$_1$–C$_6$)alkylsulphonyl groups, a formyl group, trifluoro(C$_1$–C$_6$)alkylcarbonyl groups, (C$_1$–C$_6$)alkylcarboxyl groups, a thiocarbamyl group, and Z groups, and said substituted amino may constitute a ring chosen from 5- and 6-membered rings containing at least one heteroatom wherein one of said at least one heteroatoms is the nitrogen atom of said amino;

R$_6$ is chosen from C$_1$–C$_6$ alkyl groups; C$_1$–C$_6$ monohydroxyalkyl groups; C$_2$–C$_6$ polyhydroxyalkyl groups; a group Z;(C$_1$–C$_6$)alkoxy(C$_1$–C$_6$)alkyl groups; aryl groups; a benzyl group; carboxy(C$_1$–C$_6$)alkyl groups; (C$_1$–C$_6$)alkylcarboxy-(C$_1$–C$_6$)alkyl groups; cyano(C$_1$–C$_6$)alkyl groups; carbamyl(C$_1$–C$_6$)alkyl groups; N—(C$_1$–C$_6$)alkylcarbamyl(C$_1$–C$_6$)alkyl groups; N,N-di(C$_1$–C$_6$)alkylcarbamyl(C$_1$–C$_6$)alkyl groups; C$_1$–C$_6$ trifluoroalkyl groups; C$_1$–C$_6$ aminosulphonylalkyl groups; C$_1$–C$_6$ N—Z-aminosulphonylalkyl groups; N—(C$_1$–C$_6$)alkylaminosulphonyl(C$_1$–C$_6$)alkyl groups; N,N-di(C$_1$–C$_6$)alkylaminosulphonyl(C$_1$–C$_6$)alkyl groups; (C$_1$–C$_6$)alkylsulphinyl(C$_1$–C$_6$)alkyl groups; (C$_1$–C$_6$)alkylsulphonyl(C$_1$–C$_6$)alkyl groups;(C$_1$–C$_6$)alkylcarbonyl(C$_1$–C$_6$)alkyl groups; C$_1$–C$_6$ aminoalkyl groups; C$_1$–C$_6$ aminoalkyl groups wherein said alkyl is optionally substituted with at least one hydroxyl group and wherein said amino is substituted with one or two groups, which may be identical or different, chosen from C$_1$–C$_6$ alkyl groups, C$_1$–C$_6$ monohydroxyalkyl groups, C$_2$–C$_6$ polyhydroxyalkyl groups, (C$_1$–C$_6$) alkylcarbonyl groups, a formyl group, trifluoro-(C$_1$–C$_6$)alkylcarbonyl groups, (C$_1$–C$_6$)alkylcarboxyl groups, a carbamyl group, N—(C$_1$–C$_6$)alkylcarbamyl groups, N,N-di-(C$_1$–C$_6$)alkylcarbamyl groups, a thiocarbamyl group, C$_1$–C$_6$ alkylsulphonyl groups, Z groups, and said substituted amino may constitute a ring chosen from 5- and 6-membered rings containing at least one heteroatom wherein one of said at least one heteroatoms is the nitrogen atom of said amino;

A is chosen from —NR$_4$R$_5$ groups and a hydroxyl group; A' is chosen from —NR'$_4$R'$_5$ groups and a hydroxyl group;

R$_4$, R$_5$, R'$_4$ and R'$_5$, which may be identical or different, are each chosen from hydrogen; Z groups; C$_1$–C$_6$ alkyl groups; C$_1$–C$_6$ monohydroxyalkyl groups; C$_2$–C$_6$ polyhydroxyalkyl groups; (C$_1$–C$_6$)alkoxy(C$_1$–C$_6$)alkyl groups; aryl groups; a benzyl group; cyano(C$_1$–C$_6$) alkyl groups; carbamyl(C$_1$–C$_6$)alkyl groups; N—(C$_1$–C$_6$)alkylcarbamyl(C$_1$–C$_6$)alkyl groups; N,N-di(C$_1$–C$_6$)alkylcarbamyl(C$_1$–C$_6$)alkyl groups; thiocarbamyl(C$_1$–C$_6$)alkyl groups; C$_1$–C$_6$ trifluoroalkyl groups; C$_1$–C$_6$sulphoalkyl groups; (C$_1$–C$_6$) alkylcarboxy(C$_1$–C$_6$)alkyl groups; (C$_1$–C$_6$) alkylsulphinyl(C$_1$–C$_6$)alkyl groups; C$_1$–C$_6$ aminosulphonylalkyl groups; C$_1$–C$_6$ N—Z-aminosulphonylalkyl groups; N—(C$_1$–C$_6$)alkylaminosulphonyl(C$_1$–C$_6$)alkyl groups; N,N-di(C$_1$–C$_6$)alkylaminosulphonyl(C$_1$–C$_6$)alkyl groups; (C$_1$–C$_6$)alkylcarbonyl(C$_1$–C$_6$)alkyl groups; C$_1$–C$_6$aminoalkyl groups wherein said alkyl is optionally substituted with at least one hydroxyl group; C$_1$–C$_6$aminoalkyl groups wherein said alkyl is optionally substituted with at least one hydroxyl group and wherein said amino is substituted with one or two groups, which may be identical or different, chosen from C$_1$–C$_6$ alkyl groups, C$_1$–C$_6$ monohydroxyalkyl groups, C$_2$–C$_6$ polyhydroxyalkyl groups, (C$_1$–C$_6$) alkylcarbonyl groups, a carbamyl group, N—(C$_1$–C$_6$) alkylcarbamyl groups, N,N-di(C$_1$–C$_6$)alkylcarbamyl groups, (C$_1$–C$_6$)alkylsulphonyl groups, a formyl group, trifluoro(C$_1$–C$_6$)alkylcarbonyl groups, (C$_1$–C$_6$) alkylcarboxyl groups, thiocarbamyl groups, groups Z, and said substituted amino may constitute a ring chosen from 5- and 6-membered rings containing at least one heteroatom wherein one of said at least one heteroatoms is the nitrogen atom of said amino;

Z, which may be identical or different, is chosen from unsaturated cationic groups of formula (II), unsaturated cationic groups of formula (III), and saturated cationic groups of formula (IV):

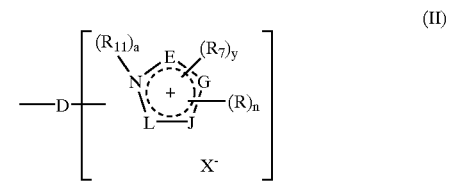

(II)

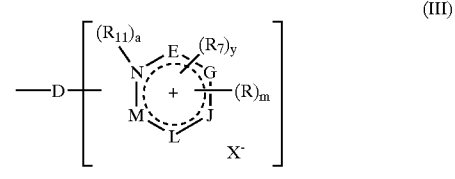

(III)

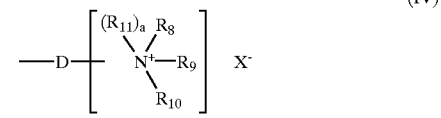

(IV)

wherein:

D is a linker arm chosen form linear and branched divalent alkyl chains, wherein said linear and branched divalent alkyl chains can be interrupted by at least one heteroatom, and further wherein said linear and branched divalent alkyl chains can be (C$_1$–C$_6$)alkylsulphonyl groups, a formyl group, trifluoro(C$_1$–C$_6$)alkylcarbonyl groups, (C$_1$–C$_6$) alkylcarboxyl groups, thiocarbamyl groups, groups Z, and said substituted amino may constitute a ring chosen from 5- and 6-membered rings containing at least one heteroatom wherein one of said at least one heteroatoms is the nitrogen atom of said amino;

Z, which may be identical or different, is chosen from unsaturated cationic groups of formula (II), unsaturated cationic groups of formula (III), and saturated cationic groups of formula (IV):

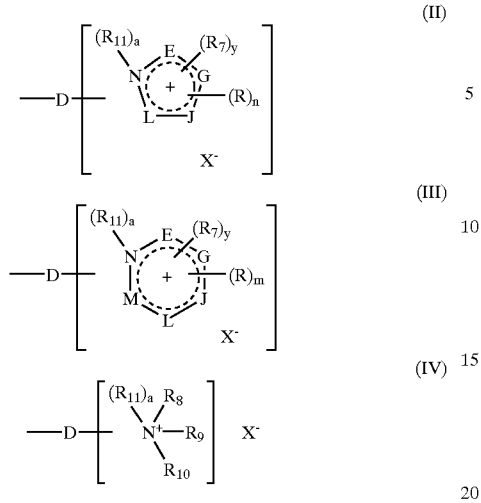

wherein:
D is a linker arm chosen form linear and branched divalent alkyl chains, wherein said linear and branched divalent alkyl chains can be interrupted by at least one heteroatom, and further wherein said linear and branched divalent alkyl chains can be substituted with at least one group chosen from a hydroxyl group and $C_1$–$C_6$ alkoxy groups, further wherein said linear and branched divalent alkyl chains can bear at least one ketone function;

ring members E, A, J, L and M, which may be identical or different, are each chosen from carbon, oxygen, sulphur and nitrogen;

n is an integer ranging from 0 to 4 inclusive;

m is an integer ranging from 0 to 5 inclusive;

the groups R, which may be identical or different, are each chosen from additional Z groups which may be identical to or different from other Z groups, halogens, hydroxyl groups, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri($C_1$–$C_6$)alkylsilane($C_1$–$C_6$)alkyl groups, an amido group, an aldehydo group, a carboxyl group, ($C_1$–$C_6$)alkylcarbonyl groups, a thio group, $C_1$–$C_6$ thioalkyl groups, $C_1$–$C_6$ alkylthio groups, an amino group, amino groups protected with at least one group chosen from ($C_1$–$C_6$) alkylcarbonyl groups, a carbamyl group, and $C_1$–$C_6$ alkylsulphonyl groups, and NHR" groups and NR"R'" groups wherein R" and R'", which may be identical or different, are each chosen from $C_1$–$C_6$ alkyl groups, $C_1$–$C_6$ monohydroxyalkyl groups and $C_2$–$C_6$ polyhydroxyalkyl groups;

$R_7$ is chosen from $C_1$–$C_6$ alkyl groups, $C_1$–$C_6$ monohydroxyalkyl groups, $C_2$–$C_6$ polyhydroxyalkyl groups, cyano($C_1$–$C_6$)alkyl groups, tri($C_1$–$C_6$)alkylsilane($C_1$–$C_6$)alkyl groups, ($C_1$–$C_6$)alkoxy ($C_1$–$C_6$)alkyl groups, carbamyl-($C_1$–$C_6$)alkyl groups, ($C_1$–$C_6$)alkylcarboxy($C_1$–$C_6$)alkyl groups, a benzyl group and an additional Z group which may be identical to or different from other Z groups;

$R_8$, $R_9$ and $R_{10}$, which may be identical or different, are each chosen from $C_1$–$C_6$ alkyl groups, $C_1$–$C_6$ monohydroxyalkyl groups, $C_2$–$C_6$ polyhydroxyalkyl groups, ($C_1$–$C_6$)alkoxy($C_1$–$C_6$)alkyl groups, cyano($C_1$–$C_6$)alkyl groups, aryl groups, a benzyl group, $C_1$–$C_6$ amidoalkyl groups, tri($C_1$–$C_6$) alkylsilane($C_1$–$C_6$)alkyl groups, and $C_1$–$C_6$ aminoalkyl groups wherein said amino is protected with at least one group chosen from ($C_1$–$C_6$) alkylcarbonyl groups, a carbamyl group and $C_1$–$C_6$ alkylsulphonyl groups; two of said groups $R_8$, $R_9$ and $R_{10}$ can together optionally form, with the nitrogen atom to which they are attached, a saturated ring chosen from 5 and 6-membered carbon-based rings containing at least one heteroatom, wherein said ring is optionally substituted with at least one group chosen from halogens, a hydroxyl group, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri($C_1$–$C_6$)alkylsilane($C_1$–$C_6$)alkyl groups, an amido group, an aldehydo group, a carboxyl group, keto($C_1$–$C_6$)alkyl groups, a thio group, $C_1$–$C_6$ thioalkyl group, $C_1$–$C_6$ alkylthio groups, an amino group, and amino groups protected with at least one group chosen from ($C_1$–$C_6$) alkylcarbonyl groups, a carbamyl group and $C_1$–$C_6$ alkylsulphonyl groups;

one of said groups $R_8$, $R_9$ and $R_{10}$ is optionally an additional Z group which may be identical to or different from other Z groups;

$R_{11}$ is chosen from $C_1$–$C_6$ alkyl groups, $C_1$–$C_6$ monohydroxyalkyl groups, $C_2$–$C_6$ polyhydroxyalkyl groups, aryl groups, a benzyl group, $C_1$–$C_6$ aminoalkyl groups, carboxy($C_1$–$C_6$)alkyl groups, cyano($C_1$–$C_6$)alkyl groups, carbamyl($C_1$–$C_6$) alkyl groups, $C_1$–$C_6$ trifluoroalkyl groups, tri ($C_1$–$C_6$)alkylsilane($C_1$–$C_6$)alkyl groups, $C_1$–$C_6$ sulphonamidoalkyl groups, ($C_1$–$C_6$)alkylcarboxy ($C_1$–$C_6$)alkyl groups, ($C_1$–$C_6$)alkylsulphinyl ($C_1$–$C_6$)alkyl groups, ($C_1$–$C_6$)alkylsulphonyl ($C_1$–$C_6$)alkyl groups, ($C_1$–$C_6$)alkylketo($C_1$–$C_6$) alkyl groups, N—($C_1$–$C_6$)alkylcarbamyl($C_1$–$C_6$) alkyl groups, N—($C_1C_6$)alkylsulphonamido ($C_1$–$C_6$)alkyl groups, and $C_1$–$C_6$ aminoalkyl groups wherein said amino is protected with at least one group chosen from ($C_1$–$C_6$) alkylcarbonyl groups, a carbamyl group and $C_1$–$C_6$ alkylsulphonyl groups; and a and y, which may be identical or different, are integers chosen from 0 and 1, X⁻ is chosen from monovalent anions and divalent anions;

wherein in said compound of formula (I), at least one of $R_1$, $R_2$, $R_3$, and A comprises at least one Z group; and provided that:

when Z is an unsaturated cationic group of formula (II):
if a=0, then said linker arm D is attached to said nitrogen atom other than E, G, J, and L,
if a=1, then said linker arm D is attached to one of said ring members chosen from E, G, J and L,
y=1 only when:
1) said ring members E, G, J, and L are all simultaneously carbon atoms and $R_7$ is attached to said nitrogen atom of the unsaturated ring; or alternatively
2) at least one of the ring members E, G, J, and L is a nitrogen atom to which $R_7$ is attached;

when Z is an unsaturated cationic group of formula (III):
if a=0, then said linker arm D is attached to said nitrogen atom other than E, G, J, L, and M, if a=1, then said linker arm D is attached to one of said ring members chosen from E, G, J, L, and M, y=1 only when at least one of said ring members E, G, J, L and M is a divalent atom and $R_7$ is attached to said nitrogen atom of the unsaturated ring other than E, G, J, L and M; and when Z is a cationic group of formula (IV):
if a=0, then the linker arm D is attached to the nitrogen atom bearing said groups $R_8$, $R_9$ and $R_{10}$;

if a=1, then two of said groups $R_8$, $R_9$ and $R_{10}$ form, together with the nitrogen atom to which they are attached, a saturated ring chosen from a 5 and 6-membered rings as defined above, and said linker arm D is attached to a carbon atom of said saturated ring.

12. A composition for dyeing keratin fibers comprising, in a medium suitable for dyeing, at least one oxidation precursor chosen from compounds of formula (I) and acid addition salts thereof:

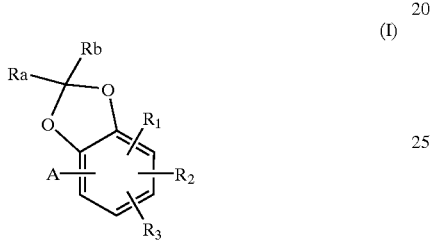

(I)

wherein:
Ra and Rb, which may be identical or different, are each chosen from hydrogen, $C_1$–$C_6$ alkyl groups, $C_1$–$C_6$ hydroxyalkyl groups, and together can form, with the carbon atom to which they are attached, a saturated ring chosen from 5, 6- and 7-membered carbon-based rings;

$R_1$, $R_2$ and $R_3$, which may be identical or different, are each chosen from hydrogen; halogens; Z groups; A' groups; ($C_1$–$C_6$)alkylcarbonyl groups; amino($C_1$–$C_6$) alkylcarbonyl groups; N—Z-amino($C_1$–$C_6$) alkylcarbonyl groups; N—($C_1$–$C_6$)alkylamino($C_1$–$C_6$) alkylcarbonyl groups; N,N-di($C_1$–$C_6$)alkylamino ($C_1$–$C_6$)alkylcarbonyl groups; amino($C_1$–$C_6$) alkylcarbonyl($C_1$–$C_6$)alkyl groups; N—Z-amino ($C_1$–$C_6$)alkylcarbonyl($C_1$–$C_6$)alkyl groups; N—($C_1$–$C_6$)alkylamino($C_1$–$C_6$)alkylcarbonyl($C_1$–$C_6$) alkyl groups; N,N-di($C_1$–$C_6$)alkylamino($C_1$–$C_6$) alkylcarbonyl($C_1$–$C_6$)alkyl groups; a carboxyl group; ($C_1$–$C_6$)alkylcarboxyl groups; $C_1$–$C_6$alkylsulphonyl groups; aminosulphonyl groups; N—Z-aminosulphonyl groups; $C_1$–$C_6$N-alkylaminosulphonyl groups; N,N-di($C_1$–$C_6$)alkylaminosulphonyl groups; $C_1$–$C_6$ aminosulphonylalkyl groups; $C_1$–$C_6$ N—Z-aminosulphonylalkyl groups; N—($C_1$–$C_6$) alkylaminosulphonyl($C_1$–$C_6$)alkyl groups; N,N-di ($C_1$–$C_6$)alkylaminosulphonyl($C_1$–$C_6$)alkyl groups; a carbamyl group N—($C_1$–$C_6$)alkylcarbamyl groups; N,N-di($C_1$–$C_6$)alkylcarbamyl groups; carbamyl ($C_1$–$C_6$)alkyl groups: N—($C_1$–$C_6$)alkylcarbamyl ($C_1$–$C_6$)alkyl groups; N,N-di($C_1$–$C_6$)alkylcarbamyl ($C_1$–$C_6$)alkyl groups; $C_1$–$C_6$ alkyl groups; $C_1$–$C_6$ monohydroxyalkyl groups; $C_2$–$C_6$ polyhydroxyalkyl groups; ($C_1$–$C_6$)alkoxy($C_1$–$C_6$)alkyl groups; $C_1$–$C_6$trifluoroalkyl groups; a cyano group; groups —$OR_6$; groups —$SR_6$; $C_1$–$C_6$aminoalkyl groups wherein said alkyl is optionally substituted with at least one hydroxyl group; amino($C_1$–$C_6$)alkyl groups wherein said, alkyl component is optionally substituted with at least one hydroxyl group and wherein said amino is substituted with one or two groups, which may be identical or different, chosen from alkyl groups, $C_1$–$C_6$ monohydroxyalkyl groups, $C_2$–$C_6$ polyhydroxyalkyl groups, ($C_1$–$C_6$)alkylcarbonyl groups, a carbamyl group, N—($C_1$–$C_6$)alkylcarbamyl groups, N,N-di($C_1$–$C_6$)alkylcarbamyl groups, ($C_1$–$C_6$) alkylsulphonyl groups, a formyl group, trifluoro ($C_1$–$C_6$)alkylcarbonyl groups, ($C_1$–$C_6$)alkylcarboxyl groups, a thiocarbamyl group, and Z groups, and said substituted amino may constitute a ring chosen from 5- and 6-membered rings containing at least one heteroatom wherein one of said at least one heteroatoms is the nitrogen atom of said amino;

$R_6$ is chosen from $C_1$–$C_6$ alkyl groups; $C_1$–$C_6$ monohydroxyalkyl groups; $C_2$–$C_6$ polyhydroxyalkyl groups; a group Z;($C_1$–$C_6$)alkoxy($C_1$–$C_6$)alkyl groups; aryl groups; a benzyl group; carboxy($C_1$–$C_6$)alkyl groups; ($C_1$–$C_6$)alkylcarboxy-($C_1$–$C_6$)alkyl groups; cyano ($C_1$–$C_6$)alkyl groups; carbamyl($C_1$–$C_6$)alkyl groups; N—($C_1$–$C_6$)alkylcarbamyl($C_1$–$C_6$)alkyl groups; N,N-di($C_1$–$C_6$)alkylcarbamyl($C_1$–$C_6$)alkyl groups; $C_1$–$C_6$trifluoroalkyl groups; $C_1$–$C_6$ aminosulphonylalkyl groups; $C_1$–$C_6$ N—Z-aminosulphonylalkyl groups; N—($C_1$–$C_6$)alkylaminosulphonyl($C_1$–$C_6$)alkyl groups; N,N-di($C_1$–$C_6$)alkylaminosulphonyl($C_1$–$C_6$) alkyl groups; ($C_1$–$C_6$)alkylsulphinyl($C_1$–$C_6$)alkyl groups; ($C_1$–$C_6$)alkylsulphonyl($C_1$–$C_6$)alkyl groups; ($C_1$–$C_6$)alkylcarbonyl($C_1$–$C_6$)alkyl groups; $C_1$–$C_6$aminoalkyl groups; $C_1$–$C_6$ aminoalkyl groups wherein said alkyl is optionally substituted with at least one hydroxyl group and wherein said amino is substituted with one or two groups, which may be identical or different, chosen from $C_1$–$C_6$ alkyl groups, $C_1$–$C_6$ monohydroxyalkyl groups, $C_2$–$C_6$ polyhydroxyalkyl groups, ($C_1$–$C_6$)alkylcarbonyl groups, a formyl group, trifluoro-($C_1$–$C_6$)alkylcarbonyl groups, ($C_1$–$C_6$) alkylcarboxyl groups, a carbamyl group, N—($C_1$–$C_6$) alkylcarbamyl groups, N,N-di-($C_1$–$C_6$)alkylcarbamyl groups, a thiocarbamyl group, $C_1$–$C_6$ alkylsulphonyl groups, Z groups, and said substituted amino may constitute a ring chosen from 5- and 6-membered rings containing at least one heteroatom wherein one of said at least one heteroatoms is the nitrogen atom of said amino;

A is chosen from —$NR_4R_5$ groups and a hydroxyl group;
A' is chosen from —$NR'_4R'_5$ groups and a hydroxyl group;

$R_4$, $R_5$, $R'_4$ and $R'_5$, which may be identical or different, are each chosen from hydrogen; Z groups; $C_1$–$C_6$ alkyl groups; $C_1$–$C_6$monohydroxyalkyl groups; $C_2$–$C_6$ polyhydroxyalkyl groups; ($C_1$–$C_6$)alkoxy($C_1$–$C_6$)alkyl groups; aryl groups; a benzyl group; cyano($C_1$–$C_6$) alkyl groups; carbamyl($C_1$–$C_6$)alkyl groups; N—($C_1$–$C_6$)alkylcarbamyl($C_1$–$C_6$)alkyl groups; N,N-di($C_1$–$C_6$)alkylcarbamyl($C_1$–$C_6$)alkyl groups; thiocarbamyl($C_1$–$C_6$)alkyl groups; $C_1$–$C_6$ trifluoroalkyl groups; $C_1$–$C_6$ sulphoalkyl groups; ($C_1$–$C_6$) alkylcarboxy($C_1$–$C_6$)alkyl groups; ($C_1$–$C_6$) alkylsulphinyl($C_1$–$C_6$)alkyl groups; $C_1$–$C_6$ aminosulphonylalkyl groups; $C_1$–$C_6$ N—Z-aminosulphonylalkyl groups; N—($C_1$–$C_6$) alkylaminosulphonyl($C_1$–$C_6$)alkyl groups; N,N-di ($C_1$–$C_6$)alkylaminosulphonyl($C_1$–$C_6$)alkyl groups; ($C_1$–$C_6$)alkylcarbonyl($C_1$–$C_6$)alkyl groups; $C_1$–$C_6$ aminoalkyl groups wherein said alkyl is optionally substituted with at least one hydroxyl group; $C_1$–$C_6$ aminoalkyl groups wherein said alkyl is optionally substituted with at least one hydroxyl group and wherein said amino is substituted with one or two groups, which may be identical or different, chosen from $C_1$–$C_6$alkyl groups, $C_1$–$C_6$ monohydroxyalkyl groups, $C_2$–$C_6$ polyhydroxyalkyl groups, ($C_1$–$C_6$)alkylcarbonyl groups, a carbamyl group, N—($C_1$–$C_6$) alkylcarbamyl groups, N,N-di($C_1$–$C_6$)alkylcarbamyl groups, ($C_1$–$C_6$)alkylsulphonyl groups, a formyl group, trifluoro($C_1$–$C_6$)alkylcarbonyl groups, ($C_1$–$C_6$) alkylcarboxyl groups, thiocarbamyl groups, groups Z, and said substituted amino may constitute a ring chosen from 5- and 6-membered rings containing at least one heteroatom wherein one of said at least one heteroatoms is the nitrogen atom of said amino;

Z, which may be identical or different, is chosen from unsaturated cationic groups of formula (II), unsaturated cationic groups of formula (III), and saturated cationic groups of formula (IV),

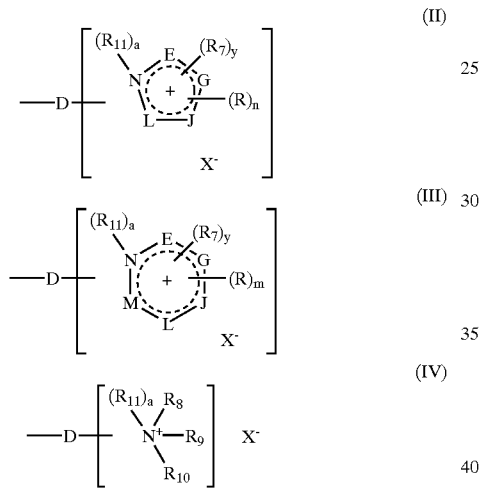

wherein:
D is a linker arm chosen form linear and branched divalent alkyl chains, wherein said linear and branched divalent alkyl chains can be interrupted by at least one heteroatom, and further wherein said linear and branched divalent alkyl chains can be substituted with at least one group chosen from a hydroxyl group and $C_1$–$C_6$ alkoxy groups, further wherein said linear and branched divalent alkyl chains can bear at least one ketone function;

ring members E, G, J, L and M, which may be identical or different, are each chosen from carbon, oxygen, sulphur and nitrogen;

n is an integer ranging from 0 to 4 inclusive;
m is an integer ranging from 0 to 5 inclusive;
the groups R, which may be identical or different, are each chosen from additional Z groups which may be identical to or different from other Z groups, halogens, hydroxyl groups, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri($C_1$–$C_6$)alkylsilane($C_1$–$C_6$)alkyl groups, an amido group, an aldehydo group, a carboxyl group, ($C_1$–$C_6$) alkylcarbonyl groups, a thio group, $C_1$–$C_6$ thioalkyl groups, $C_1$–$C_6$ alkylthio groups, an amino group, amino groups protected with at least one group chosen from ($C_1$–$C_6$)alkylcarbonyl groups, a carbamyl group, and $C_1$–$C_6$ alkylsulphonyl groups, and NHR" groups and NR"R'" groups wherein R" and R'", which may be identical or different, are each chosen from $C_1$–$C_6$alkyl groups, $C_1$–$C_6$ monohydroxyalkyl groups and $C_2$–$C_6$ polyhydroxyalkyl groups;

$R_7$ is chosen from $C_1$–$C_6$alkyl groups, $C_1$–$C_6$ monohydroxyalkyl groups, $C_2$–$C_6$ polyhydroxyalkyl groups, cyano($C_1$–$C_6$)alkyl groups, tri($C_1$–$C_6$) alkylsilane($C_1$–$C_6$)alkyl groups, ($C_1$–$C_6$)alkoxy ($C_1$–$C_6$)alkyl groups, carbamyl-($C_1$–$C_6$)alkyl groups, ($C_1$–$C_6$)alkylcarboxy($C_1$–$C_6$)-alkyl groups, a benzyl group and an additional Z group which may be identical to or different from other Z groups;

$R_8$, $R_9$ and $R_{10}$, which may be identical or different, are each chosen from $C_1$–$C_6$ alkyl groups, $C_1$–$C_6$ monohydroxyalkyl groups, $C_2$–$C_6$ polyhydroxyalkyl groups, ($C_1$–$C_6$)alkoxy($C_1$–$C_6$)alkyl groups, cyano ($C_1$–$C_6$)alkyl groups, aryl groups, a benzyl group, $C_1$–$C_6$ amidoalkyl groups, tri($C_1$–$C_6$)alkylsilane ($C_1$–$C_6$)alkyl groups, and $C_1$–$C_6$ aminoalkyl groups wherein said amino is protected with at least one group chosen from ($C_1$–$C_6$)alkylcarbonyl groups, a carbamyl group and $C_1$–$C_6$ alkylsulphonyl groups; two of said groups $R_8$, $R_9$ and $R_{10}$ can together optionally form, with the nitrogen atom to which they are attached, a saturated ring chosen from 5- and 6-membered carbon-based rings containing at least one heteroatom, wherein said ring is optionally substituted with at least one group chosen from halogens, a hydroxyl group, $C_1$–$C_6$alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri($C_1$–$C_6$)alkylsilane($C_1$–$C_6$)alkyl groups, an amido group, an aldehydo group, a carboxyl group, keto ($C_1$–$C_6$)alkyl groups, a thio group, $C_1$–$C_6$ thioalkyl groups, $C_1$–$C_6$ alkylthio groups, an amino group, and amino groups protected with at least one group chosen from ($C_1$–$C_6$)alkylcarbonyl groups, a carbamyl group and $C_1$–$C_6$ alkylsulphonyl groups;

one of said groups $R_8$, $R_9$ and $R_{10}$ is optionally an additional Z group which may be identical to or different from other Z groups;

$R_{11}$ is chosen from $C_1$–$C_6$ alkyl groups, $C_1$–$C_6$ monohydroxyalkyl groups, $C_2$–$C_6$ polyhydroxyalkyl groups, aryl groups, a benzyl group, $C_1$–$C_6$ aminoalkyl groups, carboxy($C_1$–$C_6$)alkyl groups, cyano ($C_1$–$C_6$)alkyl groups, carbamyl($C_1$–$C_6$)alkyl groups, $C_1$–$C_6$ trifluoroalkyl groups, tri($C_1$–$C_6$)alkylsilane ($C_1$–$C_6$)alkyl groups, $C_1$–$C_6$ sulphonamidoalkyl groups, ($C_1$–$C_6$)alkylcarboxy($C_1$–$C_6$)alkyl groups, ($C_1$–$C_6$)alkylsulphinyl($C_1$–$C_6$)alkyl groups, ($C_1$–$C_6$) alkylsulphonyl($C_1$–$C_6$)alkyl groups,($C_1$–$C_6$) alkylketo($C_1$–$C_6$)alkyl groups, N—($C_1$–$C_6$) alkylcarbamyl($C_1$–$C_6$)alkyl groups, N—($C_1$–$C_6$) alkylsulphonamido($C_1$–$C_6$)alkyl groups, and $C_1$–$C_6$ aminoalkyl groups wherein said amino is protected with at least one group chosen from ($C_1$–$C_6$) alkylcarbonyl groups, a carbamyl group and $C_1$–$C_6$ alkylsulphonyl groups; and a and y, which may be identical or different, are integers chosen from 0 and 1;

$X^-$ is chosen from monovalent anions and divalent anions;

wherein in said compound of formula (I), at least one of $R_1$, $R_2$, $R_3$, and A comprises at least one Z group; and provided that:
    when Z is an unsaturated cationic group of formula (II):
        if a=0, then said linker arm D is attached to said nitrogen atom other than E, G, J, and L,
        if a=1, then said linker arm D is attached to one of said ring members chosen from E, G, J and L,
        y=1 only when:
            1) said ring members E, G, J, and L are all simultaneously carbon atoms and $R_7$ is attached to said nitrogen atom of the unsaturated ring; or alternatively
            2) at least one of the ring members E, G, J, and L is a nitrogen atom to which $R_7$ is attached;
    when Z is an unsaturated cationic group of formula (III):
        if a=0, then said linker arm D is attached to said nitrogen atom other than E, G, J, L, and M,
        if a=1, then said linker arm D is attached to one of said ring members chosen from E, G, J, L, and M,
        y=1 only when at least one of said ring members E, G, J, L and M is a divalent atom and $R_7$ is attached to said nitrogen atom of the unsaturated ring other than E, G, J, L and M; and
    when Z is a cationic group of formula (IV):
        if a=0, then the linker arm D is attached to the nitrogen atom bearing said groups $R_8$, $R_9$ and $R_{10}$;
        if a=1, then two of said groups $R_8$, $R_9$ and $R_{10}$ form, together with the nitrogen atom to which they are attached, a saturated ring chosen from a 5- and 6-membered rings as defined above, and said linker arm D is attached to a carbon atom of said saturated ring.

13. A composition according to claim 12, wherein said at least one oxidation dye precursor is present in a concentration ranging from 0.0005 to 12% by weight relative to the total weight of said composition.

14. A composition according to claim 13, wherein said concentration ranges from 0.005% to 6% by weight relative to the total weight of said composition.

15. A composition according to claim 12, further comprising at least one oxidation base chosen from para-phenylenediamine bases, bis(phenyl)alkylenediamine bases, para-aminophenol bases, ortho-aminophenol bases and heterocyclic bases.

16. A composition according to claim 15, wherein said para-phenylenediamines are chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and acid addition salts thereof.

17. A composition according to claim 15, wherein said bis(phenyl)alkylenediamines are chosen from N,NN-bis(β-hydroxyethyl)-N,NN-bis(4N-aminophenyl)-1,3-diaminopropanol, N,NN-bis(β-hydroxyethyl)-N,NN-bis(4N-aminophenyl)ethylenediamine, N,NN-bis(4-aminophenyl)tetramethylenediamine, N,NN-bis(β-hydroxyethyl)-N,NN-bis(4-aminophenyl)tetramethylenediamine, N,NN-bis(4-methylaminophenyl)tetramethylenediamine, N,NN-bis(ethyl)-N,NN-bis(4N-amino-3N-methylphenyl)ethylenediamine, 1,8-bis(2,5-diaminophenoxy)-3,5-dioxaoctane, and acid addition salts thereof.

18. A composition according to claim 15, wherein said para-aminophenols are chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and acid addition salts thereof.

19. A composition according to claim 15, wherein said ortho-aminophenols are chosen from 2-aminophenol, 2-amino-5-methylphenol, 2-amino-6-methylphenol, 5-acetamido-2-aminohenol, and acid addition salts thereof.

20. A composition according to claim 15, wherein said heterocyclic bases are chosen from pyridines, pyrimidines, and pyrazoles.

21. A composition according to claim 15, wherein said oxidation base is present in a concentration ranging from 0.0005 to 12% by weight relative to the total weight of said composition.

22. A composition according to claim 21, wherein said concentration ranges from 0.005% to 6% by weight relative to the total weight of said composition.

23. A composition according to claim 12, further comprising at least one coupler.

24. A composition according to claim 23, wherein said at least one coupler is chosen from meta-phenylenediamines, meta-aminophenols, meta-diphenols, heterocyclic couplers, and acid addition salts thereof.

25. A composition according to claim 23, wherein said at least one coupler is chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one and acid addition salts thereof.

26. A composition according to claim 23, wherein said at least one coupler is present in a concentration ranging from 0.0001% to 10% by weight relative to the total weight of said composition.

27. A composition according to claim 26, wherein said concentration ranges from 0.005% to 5% by weight relative to the total weight of said composition.

28. A composition according to claim 12, further comprising at least one direct dye.

29. A composition according to claim 12, wherein said medium is chosen from water and a mixture of water and at least one organic solvent chosen from $C_1$–$C_4$ lower alkanols, glycerol, glycols, glycol ethers, aromatic alcohols, and mixtures thereof.

30. A composition according to claim 28, wherein said at least one organic solvent is present in an amount ranging from about 1% to 40% by weight relative to the total weight of said composition.

31. A composition according to claim 12, further comprising at least one adjuvant chosen from anionic surfactants, cationic surfactants, nonionic surfactants, amphoteric surfactants, zwitterionic surfactants, anionic polymers, cationic polymers, nonionic polymers, amphoteric polymers, zwitterionic polymers, inorganic thickeners, organic thickeners, antioxidants, penetration agents, sequestering agents, fragrances, buffers, dispersing agents, packaging agents, silicones, film-forming agents, ceramides, preserving agents and opacifiers.

32. A composition according to claim 12, further comprising at least one agent chosen from acidifying agents and basifying agents.

33. A composition according to claim 12, having a pH ranging from 3 to 12.

34. A composition according to claim 12, said composition being in a form chosen from liquids, creams and gels.

35. A composition according to claim 12, wherein said acid addition salt is chosen from a hydrochloride, a hydrobromide, a sulphate, a citrate, a succinate, a tartrate, a lactate and an acetate.

36. A process for oxidation dyeing of keratin fibres, comprising applying to said keratin fibres at least one dye composition for a period sufficient to develop a desired coloration, said applying being carried out in the presence of air without additional oxidizing agent being present or in the presence of at least one oxidizing agent other than air or in addition to air, said dye composition comprising, in a medium suitable for dyeing, at least one oxidation precursor chosen from compounds of formula (I) and acid addition salts thereof:

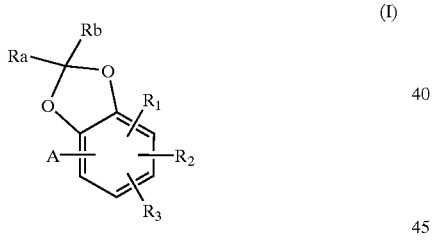

(I)

wherein:
Ra and Rb, which may be identical or different, are each chosen from hydrogen, $C_1$–$C_6$ alkyl groups, $C_1$–$C_6$ hydroxyalkyl groups, and together can form, with the carbon atom to which they are attached, a saturated ring chosen from 5-, 6- and 7-membered carbon-based rings;

$R_1$, $R_2$ and $R_3$, which may be identical or different, are each chosen from hydrogen; halogens; Z groups; A' groups; ($C_1$–$C_6$)alkylcarbonyl groups; amino($C_1$–$C_6$)alkylcarbonyl groups; N—Z-amino($C_1$–$C_6$)alkylcarbonyl groups; N—($C_1$–$C_6$)alkylamino($C_1$–$C_6$)alkylcarbonyl groups; N,N-di($C_1$–$C_6$)alkylamino($C_1$–$C_6$)alkylcarbonyl groups; amino ($C_1$–$C_6$)alkylcarbonyl($C_1$–$C_6$)alkyl groups; N—Z-amino($C_1$–$C_6$)alkylcarbonyl($C_1$–$C_6$)alkyl groups; N—($C_1$–$C_6$)alkylamino($C_1$–$C_6$)alkylcarbonyl ($C_1$–$C_6$)alkyl groups; N,N-di($C_1$–$C_6$)alkylamino ($C_1$–$C_6$)alkylcarbonyl-($C_1$–$C_6$)alkyl groups; a carboxyl group; ($C_1$–$C_6$)alkylcarboxyl groups; $C_1$–$C_6$alkylsulphonyl groups; aminosulphonyl groups; N—Z-aminosulphonyl groups; $C_1$–$C_6$ N-alkylaminosulphonyl groups; N,N-di($C_1$–$C_6$) alkylaminosulphonyl groups; $C_1$–$C_6$ aminosulphonylalkyl groups; $C_1$–$C_6$ N—Z-aminosulphonylalkyl groups; N—($C_1$–$C_6$)alkylaminosulphonyl($C_1$–$C_6$) alkyl groups; N,N-di($C_1$–$C_6$)alkylaminosulphonyl ($C_1$–$C_6$)alkyl groups; a carbamyl group; N—($C_1$–$C_6$)alkylcarbamyl groups; N,N-di($C_1$–$C_6$) alkylcarbamyl groups; carbamyl($C_1$–$C_6$)alkyl groups; N—($C_1$–$C_6$)alkylcarbamyl($C_1$–$C_6$)alkyl groups; N,N-di($C_1$–$C_6$)alkylcarbamyl($C_1$–$C_6$)alkyl groups; $C_1$–$C_6$ alkyl groups; $C_1$–$C_6$ monohydroxyalkyl groups; $C_2$–$C_6$ polyhydroxyalkyl groups; ($C_1$–$C_6$)alkoxy($C_1$–$C_6$)alkyl groups; $C_1$–$C_6$ trifluoroalkyl groups; a cyano group; groups —$OR_6$; groups —$SR_6$; $C_1$–$C_6$ aminoalkyl groups wherein said alkyl is optionally substituted with at least one hydroxyl group; amino($C_1$–$C_6$)alkyl groups wherein said alkyl component is optionally substituted with at least one hydroxyl group and wherein said amino is substituted with one or two groups, which may be identical or different, chosen from alkyl groups, $C_1$–$C_6$ monohydroxyalkyl groups, $C_2$–$C_6$ polyhydroxyalkyl groups, ($C_1$–$C_6$)alkylcarbonyl groups, a carbamyl group, N—($C_1$–$C_6$)alkylcarbamyl groups, N,N-di($C_1$–$C_6$)alkylcarbamyl groups, ($C_1$–$C_6$) alkylsulphonyl groups, a formyl group, trifluoro ($C_1$–$C_6$)alkylcarbonyl groups, ($C_1$–$C_6$)alkylcarboxyl groups, a thiocarbamyl group, and Z groups, and said substituted amino may constitute a ring chosen from 5- and 6-membered rings containing at least one heteroatom wherein one of said at least one heteroatoms is the nitrogen atom of said amino;

$R_6$ is chosen from $C_1$–$C_6$ alkyl groups; $C_1$–$C_6$ monohydroxyalkyl groups; $C_2$–$C_6$ polyhydroxyalkyl groups; a group Z; ($C_1$–$C_6$)alkoxy($C_1$–$C_6$)alkyl groups; aryl groups; a benzyl group; carboxy($C_1$–$C_6$)alkyl groups; ($C_1$–$C_6$)alkylcarboxy-($C_1$–$C_6$)alkyl groups; cyano ($C_1$–$C_6$)alkyl groups; carbamyl($C_1$–$C_6$)alkyl groups; N—($C_1$–$C_6$)alkylcarbamyl($C_1$–$C_6$)alkyl groups; N,N-di($C_1$–$C_6$)alkylcarbamyl($C_1$–$C_6$)alkyl groups; $C_1$–$C_6$ trifluoroalkyl groups; $C_1$–$C_6$ aminosulphonylalkyl groups; $C_1$–$C_6$ N—Z-aminosulphonylalkyl groups; N—($C_1$–$C_6$)alkylaminosulphonyl($C_1$–$C_6$)alkyl groups; N,N-di($C_1$–$C_6$)alkylaminosulphonyl($C_1$–$C_6$)alkyl groups; ($C_1$–$C_6$)alkylsulphinyl($C_1$–$C_6$)alkyl groups; ($C_1$–$C_6$)alkylsulphonyl($C_1$–$C_6$)alkyl groups; ($C_1$–$C_6$) alkylcarbonyl($C_1$–$C_6$)alkyl groups; $C_1$–$C_6$ aminoalkyl groups; $C_1$–$C_6$ aminoalkyl groups wherein said alkyl is optionally substituted with at least one hydroxyl group and wherein said amino is substituted with one or two groups, which may be identical or different, chosen from $C_1$–$C_6$ alkyl groups, $C_1$–$C_6$ monohydroxyalkyl groups, $C_2$–$C_6$ polyhydroxyalkyl groups, ($C_1$–$C_6$) alkylcarbonyl groups, a formyl group, trifluoro-($C_1$–$C_6$)alkylcarbonyl groups, ($C_1$–$C_6$)alkylcarboxyl groups, a carbamyl group, N—($C_1$–$C_6$)alkylcarbamyl groups, N,N-di-($C_1$–$C_6$)alkylcarbamyl groups, a thiocarbamyl group, $C_1$–$C_6$ alkylsulphonyl groups, Z groups, and said substituted amino may constitute a ring chosen from 5- and 6-membered rings containing at least one heteroatom wherein one of said at least one heteroatoms is the nitrogen atom of said amino;

A is chosen from —$NR_4R_5$ groups and a hydroxyl group;

A' is chosen from —$NR'_4R'_5$ groups and a hydroxyl group;

$R_4$, $R_5$, $R'_4$ and $R'_5$ which may be identical or different, are each chosen from hydrogen; Z groups; $C_1$–$C_6$ alkyl groups; $C_1$–$C_6$ monohydroxyalkyl groups; $C_2$–$C_6$ polyhydroxyalkyl groups; ($C_1$–$C_6$)alkoxy($C_1$–$C_6$)alkyl groups; aryl groups; a benzyl group; cyano($C_1$–$C_6$)alkyl groups; carbamyl($C_1$–$C_6$)alkyl groups; N—($C_1$–$C_6$)alkylcarbamyl($C_1$–$C_6$)alkyl groups; N,N-di($C_1$–$C_6$)alkylcarbamyl($C_1$–$C_6$)alkyl groups; thiocarbamyl($C_1$–$C_6$)alkyl groups; $C_1$–$C_6$trifluoroalkyl groups; $C_1$–$C_6$ sulphoalkyl groups; ($C_1$–$C_6$) alkylcarboxy($C_1$–$C_6$)alkyl groups; ($C_1$–$C_6$) alkylsulphinyl($C_1$–$C_6$)alkyl groups; $C_1$–$C_6$ aminosulphonylalkyl groups; $C_1$–$C_6$ N—Z-aminosulphonylalkyl groups; N—($C_1$–$C_6$) alkylaminosulphonyl($C_1$–$C_6$)alkyl groups; N,N-di($C_1$–$C_6$)alkylaminosulphonyl($C_1$–$C_6$)alkyl groups; ($C_1$–$C_6$)alkylcarbonyl($C_1$–$C_6$)alkyl groups; $C_1$–$C_6$ aminoalkyl groups wherein said alkyl is optionally substituted with at least one hydroxyl group; $C_1$–$C_6$ aminoalkyl groups wherein said alkyl is optionally substituted with at least one hydroxyl group and wherein said amino is substituted with one or two groups, which may be identical or different, chosen from $C_1$–$C_6$ alkyl groups, $C_1$–$C_6$ monohydroxyalkyl groups, $C_2$–$C_6$ polyhydroxyalkyl groups, ($C_1$–$C_6$) alkylcarbonyl groups, a carbamyl group, N—($C_1$–$C_6$) alkylcarbamyl groups, N,N-di($C_1$–$C_6$)alkylcarbamyl groups, ($C_1$–$C_6$)alkylsulphonyl groups, a formyl group, trifluoro($C_1$–$C_6$)alkylcarbonyl groups, ($C_1$–$C_6$) alkylcarboxyl groups, thiocarbamyl groups, groups Z, and said substituted amino may constitute a ring chosen from 5- and 6-membered rings containing at least one heteroatom wherein one of said at least one heteroatoms is the nitrogen atom of said amino;

Z, which may be identical or different, is chosen from unsaturated cationic groups of formula (II), unsaturated cationic groups of formula (III), and saturated cationic groups of formula (IV):

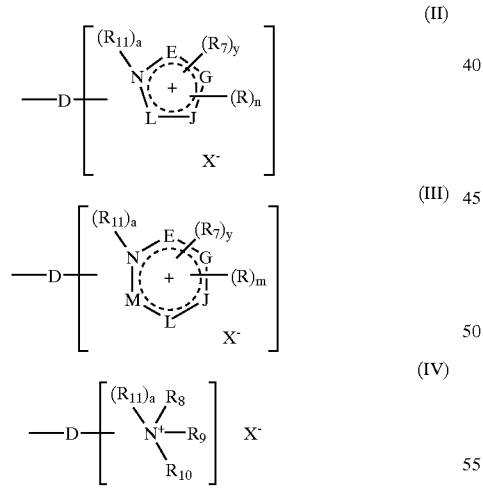

wherein:

D is a linker arm chosen form linear and branched divalent alkyl chains, wherein said linear and branched divalent alkyl chains can be interrupted by at least one heteroatom, and further wherein said linear and branched divalent alkyl chains can be substituted with at least one group chosen from a hydroxyl group and $C_1$–$C_6$ alkoxy groups, further wherein said linear and branched divalent alkyl chains can bear at least one ketone function;

ring members E, G, J, L and M, which may be identical or different, are each chosen from carbon, oxygen, sulphur and nitrogen;

n is an integer ranging from 0 to 4 inclusive;

m is an integer ranging from 0 to 5 inclusive;

the groups R, which may be identical or different, are each chosen from additional Z groups which may be identical to or different from other Z groups, halogens, hydroxyl groups, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri($C_1$–$C_6$)alkylsilane($C_1$–$C_6$)alkyl groups, an amido group, an aldehydo group, a carboxyl group, ($C_1$–$C_6$) alkylcarbonyl groups, a thio group, $C_1$–$C_6$ thioalkyl groups, $C_1$–$C_6$ alkylthio groups, an amino group, amino groups protected with at least one group chosen from ($C_1$–$C_6$)alkylcarbonyl groups, a carbamyl group, and $C_1$–$C_6$alkylsulphonyl groups, and NHR" groups and NR"R'" groups wherein R" and R'", which may be identical or different, are each chosen from $C_1$–$C_6$ alkyl groups, $C_1$–$C_6$ monohydroxyalkyl groups and $C_2$–$C_6$ polyhydroxyalkyl groups;

$R_7$ is chosen from $C_1$–$C_6$ alkyl groups, $C_1$–$C_6$ monohydroxyalkyl groups, $C_2$–$C_6$ polyhydroxyalkyl groups, cyano($C_1$–$C_6$)alkyl groups, tri($C_1$–$C_6$) alkylsilane($C_1$–$C_6$)alkyl groups, ($C_1$–$C_6$)alkoxy($C_1$–$C_6$)alkyl groups, carbamyl-($C_1$–$C_6$)alkyl groups, ($C_1$–$C_6$)alkylcarboxy($C_1$–$C_6$)-alkyl groups, a benzyl group and an additional Z group which may be identical to or different from other Z groups;

$R_8$, $R_9$ and $R_{10}$, which may be identical or different, are each chosen from $C_1$–$C_6$alkyl groups, $C_1$–$C_6$ monohydroxyalkyl groups, $C_2$$C_6$ polyhydroxyalkyl groups, ($C_1$–$C_6$)alkoxy($C_1$–$C_6$)alkyl groups, cyano($C_1$–$C_6$)alkyl groups, aryl groups, a benzyl group, $C_1$–$C_6$ amidoalkyl groups, tri($C_1$–$C_6$)alkylsilane ($C_1$–$C_6$)alkyl groups, and $C_1$–$C_6$ aminoalkyl groups wherein said amino is protected with at least one group chosen from ($C_1$–$C_6$)alkylcarbonyl groups, a carbamyl group and $C_1$–$C_6$ alkylsulphonyl groups; two of said groups $R_8$, $R_9$ and $R_{10}$ can together optionally form, with the nitrogen atom to which they are attached, a saturated ring chosen from 5- and 6-membered carbon-based rings containing at least one heteroatom, wherein said ring is optionally substituted with at least one group chosen from halogens, a hydroxyl group, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$alkoxy groups, tri ($C_1$–$C_6$)alkylsilane($C_1$–$C_6$)alkyl groups, an amido group, an aldehydo group, a carboxyl group, keto ($C_1$–$C_6$)alkyl groups, a thio group, $C_1$–$C_6$thioalkyl groups, $C_1$–$C_6$ alkylthio groups, an amino group, and amino groups protected with at least one group chosen from ($C_1$–$C_6$)alkylcarbonyl groups, a carbamyl group and $C_1$–$C_6$ alkylsulphonyl groups;

one of said groups $R_8$, $R_9$ and $R_{10}$ is optionally an additional Z group which may be identical to or different from other Z groups;

$R_{11}$ is chosen from $C_1$–$C_6$alkyl groups, $C_1$–$C_6$ monohydroxyalkyl groups, $C_2$–$C_6$ polyhydroxyalkyl groups, aryl groups, a benzyl group, $C_1$–$C_6$aminoalkyl groups, carboxy($C_1$–$C_6$)alkyl groups, cyano($C_1$–$C_6$)alkyl groups, carbamyl ($C_1$–$C_6$)alkyl groups, $C_1$–$C_6$ trifluoroalkyl groups, tri($C_1$–$C_6$)alkylsilane($C_1$–$C_6$)alkyl groups, $C_1$–$C_6$ sulphonamidoalkyl groups, ($C_1$–$C_6$)alkylcarboxy ($C_1$–$C_6$)alkyl groups, ($C_1$–$C_6$)alkylsulphinyl($C_1$–$C_6$) alkyl groups, ($C_1$–$C_6$)alkylsulphonyl($C_1$–$C_6$)alkyl groups, ($C_1$–$C_6$)alkylketo($C_1$–$C_6$)alkyl groups, N—($C_1$–$C_6$)alkylcarbamyl($C_1$–$C_6$)alkyl groups, N—($C_1$–$C_6$)alkylsulphonamido($C_1$–$C_6$)alkyl groups, and $C_1$–$C_6$ aminoalkyl groups wherein said amino is protected with at least one group chosen from ($C_1$–$C_6$)alkylcarbonyl groups, a carbamyl group and $C_1$–$C_6$ alkylsulphonyl groups; and a and y, which may be identical or different, are integers chosen from 0 and 1;

$X^-$ is chosen from monovalent anions and divalent anions;

wherein in said compound of formula (I), at least one of $R_1$, $R_2$, $R_3$, and A comprises at least one Z group; and provided that:

when Z is an unsaturated cationic group of formula (II):
  if a=0, then said linker arm D is attached to said nitrogen atom other than E, G, J, and L,
  if a=1, then said linker arm D is attached to one of said ring members chosen from E, G, J and L,
  y=1 only when:
    1) said ring members E, G, J, and L are all simultaneously carbon atoms and $R_7$ is attached to said nitrogen atom of the unsaturated ring; or alternatively
    2) at least one of the ring members E, G, J, and L is a nitrogen atom to which $R_7$ is attached;

when Z is an unsaturated cationic group of formula (III):
  if a=0, then said linker arm D is attached to said nitrogen atom other than E, G, J, L, and M,
  if a=1, then said linker arm D is attached to one of said ring members chosen from E, G, J, L, and M,
  y=1 only when at least one of said ring members E, G, J, L and M is a divalent atom and $R_7$ is attached to said nitrogen atom of the unsaturated ring other than E, G, J, L and M; and when Z is a cationic group of formula (IV):
  if a=0, then the linker arm D is attached to the nitrogen atom bearing said groups $R_8$, $R_9$ and $R_{10}$;
  if a=1, then two of said groups $R_8$, $R_9$ and $R_{10}$ form, together with the nitrogen atom to which they are attached, a saturated ring chosen from a 5- and 6-membered rings as defined above, and said linker arm D is attached to a carbon atom of said saturated ring.

37. A process according to claim 36, wherein said said applying is carried out in the presence of air without additional oxidizing agent being present.

38. A process according to claim 36, wherein said color is developed in the presence of at least one oxidizing agent added to the dye composition at the time of applying said dye composition to said keratin fibres or added separately and simultaneously with the applying of said dye composition or added separately and sequentially from the applying of said dye composition.

39. A process according to claim 38, wherein said at least one oxidizing agent is chosen from hydrogen peroxide, urea peroxide, alkali metal bromates, persalts, and enzymes.

40. A process according to claim 39, wherein said enzymes are chosen from pyranose oxidases, glucose oxidases, glycerol oxidases, lactate oxidases, pyruvate oxidases, and uricases.

41. A mutlicompartment device or multicompartment dying kit comprising a first compartment and a second compartment, wherein said second compartment comprises at least one oxidizing agent and wherein said first compartment comprises a dye composition comprising, in a medium suitable for dyeing, at least one oxidation precursor chosen from compounds of formula (I) and acid addition salts thereof:

wherein:

Ra and Rb, which may be identical or different, are each chosen from hydrogen, $C_1$–$C_6$ alkyl groups, $C_1$–$C_6$ hydroxyalkyl groups, and together can form, with the carbon atom to which they are attached, a saturated ring chosen from 5-, 6- and 7-membered carbon-based rings;

$R_1$, $R_2$ and $R_3$, which may be identical or different, are each chosen from hydrogen; halogens; Z groups; A' groups; ($C_1$–$C_6$)alkylcarbonyl groups; amino($C_1$–$C_6$) alkylcarbonyl groups; N—Z-amino($C_1$–$C_6$) alkylcarbonyl groups; N—($C_1$–$C_6$)alkylamino($C_1$–$C_6$) alkylcarbonyl groups; N,N-di($C_1$–$C_6$)alkylamino ($C_1$–$C_6$)alkylcarbonyl groups; amino($C_1$–$C_6$) alkylcarbonyl($C_1$–$C_6$)alkyl groups; N—Z-amino ($C_1$–$C_6$)alkylcarbonyl($C_1$–$C_6$)alkyl groups; N—($C_1$–$C_6$)alkylamino($C_1$–$C_6$)-alkylcarbonyl($C_1$–$C_6$) alkyl groups; N,N-di($C_1$–$C_6$)alkylamino($C_1$–$C_6$) alkylcarbonyl-($C_1$–$C_6$)alkyl groups; a carboxyl group; ($C_1$–$C_6$)alkylcarboxyl groups; $C_1$–$C_6$ alkylsulphonyl groups; aminosulphonyl groups; N—Z-aminosulphonyl groups; $C_1$–$C_6$ N-alkylaminosulphonyl groups; N,N-di($C_1$–$C_6$) alkylaminosulphonyl groups; $C_1$–$C_6$ aminosulphonylalkyl groups; $C_1$–$C_6$ N—Z-aminosulphonylalkyl groups; N—($C_1$–$C_6$) alkylaminosulphonyl($C_1$–$C_6$)alkyl groups; N,N-di ($C_1$–$C_6$)alkylaminosulphonyl($C_1$–$C_6$)alkyl groups; a carbamyl group; N—($C_1$–$C_6$)alkylcarbamyl groups; N,N-di($C_1$–$C_6$)alkylcarbamyl groups; carbamyl ($C_1$–$C_6$)alkyl groups; N—($C_1$–$C_6$)alkylcarbamyl ($C_1$–$C_6$)alkyl groups; N,N-di($C_1$–$C_6$)alkylcarbamyl ($C_1$–$C_6$)alkyl groups; $C_1$–$C_6$ alkyl groups; $C_1$–$C_6$ monohydroxyalkyl groups; $C_2$–$C_6$ polyhydroxyalkyl groups; ($C_1$–$C_6$)alkoxy($C_1$–$C_6$)alkyl groups; $C_1$–$C_6$ trifluoroalkyl groups; a cyano group; groups —$OR_6$; groups —$SR_6$; $C_1$–$C_6$ aminoalkyl groups wherein said alkyl is optionally substituted with at least one hydroxyl group; amino($C_1$–$C_6$)alkyl groups wherein said alkyl component is optionally substituted with at least one hydroxyl group and wherein said amino is substituted with one or two groups, which may be identical or different, chosen from alkyl groups, $C_1$–$C_6$ monohydroxyalkyl groups, $C_2$–$C_6$ polyhydroxyalkyl groups, ($C_1$–$C_6$)alkylcarbonyl groups, a carbamyl group, N—($C_1$–$C_6$)alkylcarbamyl groups, N,N-di ($C_1$–$C_6$)alkylcarbamyl groups, ($C_1$–$C_6$)alkylsulphonyl groups, a formyl group, trifluoro($C_1$–$C_6$)alkylcarbonyl groups, ($C_1$–$C_6$)alkylcarboxyl groups, a thiocarbamyl group, and Z groups, and said substituted amino may constitute a ring chosen from 6- and 6-membered rings containing at least one heteroatom wherein one of said at least one heteroatoms is the nitrogen atom of said amino;

$R_6$ is chosen from $C_1$–$C_6$ alkyl groups; $C_1$–$C_6$ monohydroxyalkyl groups; $C_1$–$C_6$ polyhydroxyalkyl groups; a group Z;($C_1$–$C_6$)alkoxy($C_1$–$C_6$)alkyl groups; aryl groups; a benzyl group; carboxy($C_1$–$C_6$) alkyl groups; ($C_1$–$C_6$)alkylcarboxy-($C_1$–$C_6$)alkyl groups; cyano($C_1$–$C_6$)alkyl groups; carbamyl($C_1$–$C_6$) alkyl groups; N—($C_1$–$C_6$)alkyl-carbamyl($C_1$–$C_6$)alkyl groups; N,N-di($C_1$–$C_6$)alkylcarbamyl($C_1$–$C_6$)alkyl groups; $C_1$–$C_6$ trifluoroalkyl groups; $C_1$–$C_6$ aminosulphonylalkyl groups; $C_1$–$C_6$ N—Z-aminosulphonylalkyl groups; N—($C_1$–$C_6$) alkylaminosulphonyl($C_1$–$C_6$)alkyl groups; N,N-di($C_1$–$C_6$)alkylaminosulphonyl($C_1$–$C_6$)alkyl groups; ($C_1$–$C_6$)alkylsulphinyl($C_1$–$C_6$)alkyl groups; ($C_1$–$C_6$) alkylsulphonyl($C_1$–$C_6$)alkyl groups; ($C_1$–$C_6$) alkylcarbonyl($C_1$–$C_6$)alkyl groups; $C_1$–$C_6$ aminoalkyl groups; $C_1$–$C_6$ aminoalkyl groups wherein said alkyl is optionally substituted with at least one hydroxyl group and wherein said amino is substituted with one or two groups, which may be identical or different, chosen from $C_1$–$C_6$ alkyl groups, $C_1$–$C_6$ monohydroxyalkyl groups, $C_2$–$C_6$ polyhydroxyalkyl groups, ($C_1$–$C_6$) alkylcarbonyl groups, a formyl group, trifluoro-($C_1$–$C_6$)alkylcarbonyl groups, ($C_1$–$C_6$)alkylcarboxyl groups, a carbamyl group, N—($C_1$–$C_6$)alkylcarbamyl groups, N,N-di-($C_1$–$C_6$)alkylcarbamyl groups, a thiocarbamyl group, $C_1$–$C_6$ alkylsulphonyl groups, Z groups, and said substituted amino may constitute a ring chosen from 5- and 6-membered rings containing at least one heteroatom wherein one of said at least one heteroatoms is the nitrogen atom of said amino;

A is chosen from —$NR_4R_5$ groups and a hydroxyl group;

A' is chosen from —$NR'_4R'_5$ groups and a hydroxyl group;

$R_4$, $R_5$, $R'_4$ and $R'_5$, which may be identical or different, are each chosen from hydrogen; Z groups; $C_1$–$C_6$ alkyl groups; $C_1$–$C_6$ monohydroxyalkyl groups; $C_2$–$C_6$ polyhydroxyalkyl groups; ($C_1$–$C_6$)alkoxy($C_1$–$C_6$)alkyl groups; aryl groups; a benzyl group; cyano($C_1$–$C_6$) alkyl groups; carbamyl($C_1$–$C_6$)alkyl groups; N—($C_1$–$C_6$)alkylcarbamyl($C_1$–$C_6$)alkyl groups; N,N-di($C_1$–$C_6$)alkylcarbamyl($C_1$–$C_6$)alkyl groups; thiocarbamyl($C_1$–$C_6$)alkyl groups; $C_1$–$C_6$ trifluoroalkyl groups; $C_1$–$C_6$ sulphoalkyl groups; ($C_1$–$C_6$) alkylcarboxy($C_1$–$C_6$)alkyl groups; ($C_1$–$C_6$) alkylsulphinyl($C_1$–$C_6$)alkyl groups; $C_1$–$C_6$ aminosulphonylalkyl groups; $C_1$–$C_6$ N—Z-aminosulphonylalkyl groups; N—($C_1$–$C_6$) alkylaminosulphonyl($C_1$–$C_6$)alkyl groups; N,N-di($C_1$–$C_6$)alkylaminosulphonyl($C_1$–$C_6$)alkyl groups; ($C_1$–$C_6$)alkylcarbonyl($C_1$–$C_6$)alkyl groups; $C_1$–$C_6$ aminoalkyl groups wherein said alkyl is optionally substituted with at least one hydroxyl group; $C_1$–$C_6$ aminoalkyl groups wherein said alkyl is optionally substituted with at least one hydroxyl group and wherein said amino is substituted with one or two groups, which may be identical or different, chosen from $C_1$–$C_6$ alkyl groups, $C_1$–$C_6$ monohydroxyalkyl groups, $C_2$–$C_6$ polyhydroxyalkyl groups, ($C_1$–$C_6$) alkylcarbonyl groups, a carbamyl group, N—($C_1$–$C_6$) alkylcarbamyl groups, N,N-di($C_1$–$C_6$)alkylcarbamyl groups, ($C_1$–$C_6$)alkylsulphonyl groups, a formyl group, trifluoro($C_1$–$C_6$)alkylcarbonyl groups, ($C_1$–$C_6$) alkylcarboxyl groups, thiocarbamyl groups, groups Z, and said substituted amino may constitute a ring chosen from 5- and 6-membered rings containing at least one heteratom wherein one of said at least one heteroatoms is the nitrogen atom of said amino;

Z, which may be identical or different, is chosen from unsaturated cationic groups of formula (II), unsaturated cationic groups of formula (III), and saturated cationic groups of formula (IV):

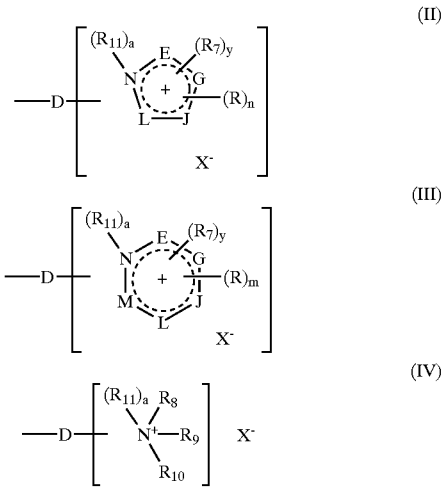

wherein:

D is a linker arm chosen form linear and branched divalent alkyl chains, wherein said linear and branched divalent alkyl chains can be interrupted by at least one heteroatom, and further wherein said linear and branched divalent alkyl chains can be substituted with at least one group chosen from a hydroxyl group and $C_1$–$C_6$ alkoxy groups, further wherein said linear and branched divalent alkyl chains can bear at least one ketone function;

ring members E, G, J, L and M, which may be identical or different, are each chosen from carbon, oxygen, sulphur and nitrogen;

n is an integer ranging from 0 to 4 inclusive;

m is an integer ranging from 0 to 5 inclusive;

the groups R, which may be identical or different, are each chosen from additional Z groups which may be identical to or different from other Z groups, halogens, hydroxyl groups, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri($C_1$–$C_6$)alkylsilane($C_1$–$C_6$)alkyl groups, an amido group, an aldehydo group, a carboxyl group, ($C_1$–$C_6$) alkylcarbonyl groups, a thio group, $C_1$–$C_6$ thioalkyl groups, $C_1$–$C_6$ alkylthio groups, an amino group, amino groups protected with at least one group chosen from ($C_1$–$C_6$)alkylcarbonyl groups, a carbamyl group, and $C_1$–$C_6$ alkylsulphonyl groups, and NHR" groups and NR"R'" groups wherein R" and R'", which may be identical or different, are each chosen from $C_1$–$C_6$ alkyl groups, $C_1$–$C_6$ monohydroxyalkyl groups and $C_2$–$C_6$ polyhydroxyalkyl groups;

$R_7$ is chosen from $C_1$–$C_6$ alkyl groups, $C_1$–$C_6$ monohydroxyalkyl groups, $C_2$–$C_6$ polyhydroxyalkyl groups, cyano($C_1$–$C_6$)alkyl groups, tri($C_1$–$C_6$)

alkylsilane($C_1$–$C_6$)alkyl groups, ($C_1$–$C_6$)alkoxy($C_1$–$C_6$)alkyl groups, carbamyl-($C_1$–$C_6$)alkyl groups, ($C_1$–$C_6$)alkylcarboxy($C_1$–$C_6$)-alkyl groups, a benzyl group and an additional Z group which may be identical to or different from other Z groups;

$R_8$, $R_9$ and $R_{10}$, which may be identical or different, are each chosen from $C_1$–$C_6$ alkyl groups, $C_1$–$C_6$ monohydroxyalkyl groups, $C_2$–$C_6$ polyhydroxyalkyl groups, ($C_1$–$C_6$)alkoxy($C_1$–$C_6$)alkyl groups, cyano($C_1$–$C_6$)alkyl groups, aryl groups, a benzyl group, $C_1$–$C_6$ amidoalkyl groups, tri($C_1$–$C_6$)alkylsilane($C_1$–$C_6$)alkyl groups, and $C_1$–$C_6$ aminoalkyl groups wherein said amino is protected with at least one group chosen from ($C_1$–$C_6$)alkylcarbonyl groups, a carbamyl group and $C_1$–$C_6$ alkylsulphonyl groups; two of said groups $R_8$, $R_9$ and $R_{10}$ can together optionally form, with the nitrogen atom to which they are attached, a saturated ring chosen from 5- and 6-membered carbon-based rings containing at least one heteroatom, wherein said ring is optionally substituted with at least one group chosen from halogens, a hydroxyl group, $C_1$–$C_6$ alkyl groups, $C_1$–$C_6$ monohydroxyalkyl groups, $C_2$–$C_6$ polyhydroxyalkyl groups, a nitro group, a cyano group, cyano($C_1$–$C_6$)alkyl groups, $C_1$–$C_6$ alkoxy groups, tri($C_1$–$C_6$)alkylsilane($C_1$–$C_6$)alkyl groups, an amido group, an aldehydo group, a carboxyl group, keto($C_1$–$C_6$)alkyl groups, a thio group, $C_1$–$C_6$ thioalkyl groups, $C_1$–$C_6$ alkylthio groups, an amino group, and amino groups protected with at least one group chosen from ($C_1$–$C_6$)alkylcarbonyl groups, a carbamyl group and $C_1$–$C_6$ alkylsulphonyl groups; one of said groups $R_8$, $R_9$ and $R_{10}$ is optionally an additional Z group which may be identical to or different from other Z groups;

$R_{11}$ is chosen from $C_1$–$C_6$ alkyl groups, $C_1$–$C_6$ monohydroxyalkyl groups, $C_2$–$C_6$ polyhydroxyalkyl groups, aryl groups, a benzyl group, $C_1$–$C_6$ aminoalkyl groups, carboxy($C_1$–$C_6$)alkyl groups, cyano($C_1$–$C_6$)alkyl groups, carbamyl($C_1$–$C_6$)alkyl groups, $C_1$–$C_6$ trifluoroalkyl groups, tri($C_1$–$C_6$)alkylsilane($C_1$–$C_6$)alkyl groups, $C_1$–$C_6$ sulphonamidoalkyl groups, ($C_1$–$C_6$)alkylcarboxy($C_1$–$C_6$)alkyl groups, ($C_1$–$C_6$)alkylsulphinyl($C_1$–$C_6$)alkyl groups, ($C_1$–$C_6$)alkylsulphonyl($C_1$–$C_6$)alkyl groups, ($C_1$–$C_6$)alkylketo($C_1$–$C_6$)alkyl groups, N—($C_1$–$C_6$)alkylcarbamyl($C_1$–$C_6$)alkyl groups, N—($C_1$–$C_6$)alkylsulphonamido($C_1$–$C_6$)alkyl groups, and $C_1$–$C_6$ aminoalkyl groups wherein said amino is protected with at least one group chosen from ($C_1$–$C_6$)alkylcarbonyl groups, a carbamyl group and $C_1$–$C_6$ alkylsulphonyl groups; and a and y, which may be identical or different, are integers chosen from 0 and 1;

$X^-$ is chosen from monovalent anions and divalent anions;

wherein in said compound of formula (I), at least one of $R_1$, $R_2$, $R_3$, and A comprises at least one Z group; and provided that:

when Z is an unsaturated cationic group of formula (II):
  if a=0, then said linker arm D is attached to said nitrogen atom other than E, G, J, and L,
  if a=1, then said linker arm D is attached to one of said ring members chosen from E, G, J and L,
  y=1 only when:
   1) said ring members E, G, J, and L are all simultaneously carbon atoms and $R_7$ is attached to said nitrogen atom of the unsaturated ring; or alternatively
   2) at least one of the ring members E, G, J, and L is a nitrogen atom to which $R_7$ is attached;

when Z is an unsaturated cationic group of formula (III):
  if a=0, then said linker arm D is attached to said nitrogen atom other than E, G, J, L, and M,
  if a=1, then said linker arm D is attached to one of said ring members chosen from E, G, J, L, and M,
  y=1 only when at least one of said ring members E, G, J, L and M is a divalent atom and $R_7$ is attached to said nitrogen atom of the unsaturated ring other than E, G, J, L and M; an when Z is a cationic group of formula (IV):
  if a=0, then the linker arm D is attached to the nitrogen atom bearing said groups $R_8$, $R_9$ and $R_{10}$;
  if a=1, then two of said groups $R_8$, $R_9$ and $R_{10}$ form, together with the nitrogen atom to which they are attached, a saturated ring chosen from a 5- and 6-membered rings as defined above, and said linker arm D is attached to a carbon atom of said saturated ring.

* * * * *

UNITED STATES PATENT AND TRADEMARK OFFICE
CERTIFICATE OF CORRECTION

PATENT NO. : 6,497,730 B1
DATED : December 24, 2002
INVENTOR(S) : Alain Genet et al.

It is certified that error appears in the above-identified patent and that said Letters Patent is hereby corrected as shown below:

Column 15,
Line 47, "-$OR_5$;" should read -- $OR_6$; --.
Line 59, "ftrifluoro($C_1$-$C_6$)alkylcarbonyl" should read
-- trifluoro($C_1$-$C_6$)alkylcarbonyl --.
Line 62, "5 and 6-membered" should read -- 5- and 6-membered --.

Column 16,
Line 28, "amino:" should read -- amino; --.
Line 63, after "at least one", delete the comma.

Column 18,
Line 1, "$C_1$-$C_6$monohydroxyalkyl" should read -- $C_1$-$C_6$ monohydroxyalkyl --.
Line 4, "$C_1$-$C_6$amidoalkyl" should read -- $C_1$-$C_6$ amidoalkyl --.
Line 15, "$C_1$-$C_6$monohydroxyalkyl" should read -- $C_1$-$C_6$ monohydroxyalkyl --.
Line 21, "$C_1$-$C_6$alkylthio" should read -- $C_1$-$C_6$ alkylthio --.
Line 64, "attached," should read -- attached; --.

Column 20,
Line 41, "halogens" should read -- halogens; --.
Line 57, "$C_1$-$C_6$aminosulphonylalkyl" should read -- $C_1$-$C_6$ aminosulphonylalkyl --.

Column 21,
Line 62, "$C_1$-$C_6$sulphoalkyl" should read -- $C_1$-$C_6$ sulphoalkyl --.

Column 22,
Line 3, "$C_1$-$C_6$aminoalkyl" should read -- $C_1$-$C_6$ aminoalkyl --.
Line 5, "$C_1$-$C_6$aminoalkyl" should read -- $C_1$-$C_6$ aminoalkyl --.
Line 50, "chosen form" should read -- chosen from --.

Column 23,
Line 23, "chosen form" should read -- chosen from --.
Line 31, "members E, A," should read -- members E, G, --.

UNITED STATES PATENT AND TRADEMARK OFFICE
CERTIFICATE OF CORRECTION

PATENT NO. : 6,497,730 B1
DATED : December 24, 2002
INVENTOR(S) : Alain Genet et al.

It is certified that error appears in the above-identified patent and that said Letters Patent is hereby corrected as shown below:

Column 24,
Line 10, "5 and 6-membered" should read -- 5- and 6-membered --.
Line 20, "$C_1$-$C_6$thioalkyl" should read -- $C_1$-$C_6$ thioalkyl --.
Lines 40-41, "N-($C_1$-$C_6$)alkylsulphonamido($C_1$-$C_6$)alkyl" should read
-- N-($C_1$-$C_6$)alkylsulphonamido($C_1$-$C_6$)alkyl --.
Line 47, "0 and l," should read -- 0 and 1; --.

Column 25,
Lines 12-13, "5 and 6-membered" should read -- 5- and 6-membered --.
Line 34, "$C_1$-$C_6$hydroxyalkyl" should read -- $C_1$-$C_6$ hydroxyalkyl --.
Line 36, "5, 6- and 7-membered" should read -- 5-, 6- and 7-membered --.
Line 50, "$C_1$-$C_6$alkylsulphonyl" should read -- $C_1$-$C_6$ alkylsulphonyl --.
Line 52, "$C_1$-$C_6$N-alkylaminosulphonyl" should read
-- $C_1$-$C_6$ N-alkylaminosulphonyl --.
Line 60, "groups:" should read -- groups; --.
Line 65, "$C_1$-$C_6$trifluoroalkyl" should read -- $C_1$-$C_6$ trifluoroalkyl --.
Line 66, "$C_1$-$C_6$aminoalkyl" should read -- $C_1$-$C_6$ aminoalkyl --.

Column 26,
Line 2, after "wherein said", delete the comma.
Line 25, "$C_1$-$C_6$trifluoroalkyl" should read -- $C_1$-$C_6$ trifluoroalkyl --.
Line 32, "$C_1$-$C_6$aminoalkyl" should read -- $C_1$-$C_6$ aminoalkyl --.
Line 53, "$C_1$-$C_6$monohydroxyalkyl" should read -- $C_1$-$C_6$ monohydroxyalkyl --.

Column 27,
Line 7, "$C_1$-$C_6$alkyl" should read -- $C_1$-$C_6$ alkyl --.
Line 21, "formula (IV)," should read -- formula (IV): --.
Line 44, "chosen form" should read -- chosen from --.

Column 28,
Lines 7, 10 and 33, "$C_1$-$C_6$alkyl" should read -- $C_1$-$C_6$ alkyl --.
Lines 56-57, "groups,($C_1$-$C_6$)alkylketo($C_1$-$C_6$)alkyl" should read -- groups, ($C_1$-$C_6$) alkylketo($C_1$-$C_6$)alkyl --.

Column 30,
Line 24, "5-acetamido-2-aminohenol," should read -- 5-acetamido-2-aminophenol, --.

UNITED STATES PATENT AND TRADEMARK OFFICE
CERTIFICATE OF CORRECTION

PATENT NO. : 6,497,730 B1
DATED : December 24, 2002
INVENTOR(S) : Alain Genet et al.

It is certified that error appears in the above-identified patent and that said Letters Patent is hereby corrected as shown below:

Column 31,
Line 67, "$C_1$-$C_6$alkylsulphonyl" should read -- $C_1$-$C_6$ alkylsulphonyl --.

Column 33,
Line 7, "$C_1$-$C_6$trifluoroalkyl" should read -- $C_1$-$C_6$ trifluoroalky l --.
Line 59, "chosen form" should read -- chosen from --.

Column 34,
Line 10, "$C_1$-$C_6$monohydroxyalkyl" should read -- $C_1$-$C_6$ monohydroxyalkyl --.
Line 12, "$C_1$-$C_6$alkoxy" should read -- $C_1$-$C_6$ alkoxy--.
Line 19, "$C_1$-$C_6$alkylsulphonyl" should read -- $C_1$-$C_6$ alkylsulphonyl --.
Line 34, "$C_1$-$C_6$alkyl" should read -- $C_1$-$C_6$ alkyl --.
Line 35, "$C_2$-$C_6$ polyhydroxyalkyl" should read -- $C_2$-$C_6$ polyhydroxyalkyl --.
Line 52, "$C_1$-$C_6$alkoxy" should read -- $C_1$-$C_6$ alkoxy --.
Line 55, "$C_1$-$C_6$thioalkyl" should read -- $C_1$-$C_6$ thioalkyl --.
Line 63, "$C_1$-$C_6$alkyl" should read -- $C_1$-$C_6$ alkyl--.
Line 66, "$C_1$-$C_6$aminoalkyl" should read -- $C_1$-$C_6$ aminoalkyl --.

Column 35,
Lines 49-50, "wherein said said applying" should read -- wherein said applying --.

Column 36,
Line 42, "$C_1$-$C_6$aminosulphonylalkyl" should read -- $C_1$-$C_6$ aminosulphonylalkyl --.
Lines 42-43, "$C_1$-$C_6$N-Z-aminosulphonylalkyl" should read
-- $C_1$-$C_6$ N-Z-aminosulphonylalkyl --.
Line 50, "$C_1$-$C_6$alkyl" should read -- $C_1$-$C_6$ alkyl --.
Line 61, "$C_1$-$C_6$monohydroxyalkyl" should read -- $C_1$-$C_6$ monohydroxyalkyl --.

Column 37,
Line 1, "6- and 6-membered" should read -- 5- and 6-membered --.
Line 6, "$C_1$-$C_6$monohydroxyalkyl" should read -- $C_1$-$C_6$ monohydroxyalkyl --.
Lines 6-7, "$C_1$-$C_6$polyhydroxyalkyl" should read -- $C_1$-$C_6$ polyhydroxyalkyl --.
Line 14, "$C_1$-$C_6$aminosulphonylalkyl" should read -- $C_1$-$C_6$ aminosulphonylalkyl --.
Line 51, "$C_1$-$C_6$aminosulphonylalkyl" should read -- $C_1$-$C_6$ aminosulphonylalkyl --.

UNITED STATES PATENT AND TRADEMARK OFFICE
CERTIFICATE OF CORRECTION

PATENT NO.      : 6,497,730 B1
DATED           : December 24, 2002
INVENTOR(S)     : Alain Genet et al.

It is certified that error appears in the above-identified patent and that said Letters Patent is hereby corrected as shown below:

Column 38,
Line 32, "chosen form" should read -- chosen from --.

Column 40,
Line 35, "M; an" should read -- M; and --.

Signed and Sealed this

Eighteenth Day of March, 2003

JAMES E. ROGAN
*Director of the United States Patent and Trademark Office*